US006980958B1

(12) United States Patent
Surwit et al.

(10) Patent No.: US 6,980,958 B1
(45) Date of Patent: Dec. 27, 2005

(54) APPARATUS AND METHODS FOR MONITORING AND MODIFYING ANTICOAGULATION THERAPY OF REMOTELY LOCATED PATIENTS

(75) Inventors: Richard S. Surwit, Chapel Hill, NC (US); Lyle M. Allen, III, Durham, NC (US); James J. Morris, Jr., Durham, NC (US); Thomas Lee Ortel, Chapel Hill, NC (US)

(73) Assignee: ZyCare, Inc., Chapel Hill, NC (US)

( * ) Notice: Subject to any disclaimer, the term of this patent is extended or adjusted under 35 U.S.C. 154(b) by 0 days.

(21) Appl. No.: 09/480,432

(22) Filed: Jan. 11, 2000

(51) Int. Cl.[7] .............................................. G06F 17/60
(52) U.S. Cl. ........................ 705/2; 600/301; 600/369
(58) Field of Search ................ 705/2–3; 600/300–301, 600/368–369

(56) References Cited

U.S. PATENT DOCUMENTS

| | | | | |
|---|---|---|---|---|
| 4,685,059 A | 8/1987 | Yamamoto | ............... | 422/82.05 |
| 4,731,726 A | 3/1988 | Allen, III | .................... | 600/300 |
| 4,803,625 A | 2/1989 | Fu et al. | ..................... | 600/483 |
| 4,981,139 A | 1/1991 | Pfohl | ......................... | 600/484 |
| 5,016,172 A | 5/1991 | Dessertine | .................. | 600/300 |
| 5,019,974 A | 5/1991 | Beckers | ...................... | 600/316 |
| 5,024,225 A | 6/1991 | Fang | .......................... | 600/301 |
| 5,025,374 A | 6/1991 | Roizen et al. | ............. | 600/300 |
| 5,047,044 A | 9/1991 | Smith et al. | ................ | 606/182 |
| 5,077,476 A | 12/1991 | Rosenthal | ............. | 250/339.09 |
| 5,078,134 A | 1/1992 | Heilman et al. | ............... | 607/4 |
| 5,216,597 A | 6/1993 | Beckers | ....................... | 356/39 |
| 5,265,613 A | 11/1993 | Feldman et al. | ............ | 600/453 |
| 5,307,263 A | 4/1994 | Brown | ...................... | 600/301 |
| 5,341,291 A | 8/1994 | Roizen et al. | ............. | 600/300 |
| 5,371,687 A | 12/1994 | Holmes, II et al. | .......... | 710/72 |
| 5,379,214 A | 1/1995 | Arbuckle et al. | .......... | 600/301 |
| 5,432,698 A | 7/1995 | Fujita | ......................... | 600/301 |
| 5,458,123 A | 10/1995 | Unger | ......................... | 600/509 |
| 5,471,382 A | 11/1995 | Tallman et al. | ............. | 600/300 |
| 5,579,775 A | 12/1996 | Dempsey et al. | ........... | 600/483 |
| 5,583,758 A * | 12/1996 | McIlroy et al. | ................ | 705/2 |
| 5,619,991 A | 4/1997 | Sloane | ....................... | 600/300 |

(Continued)

FOREIGN PATENT DOCUMENTS

EP 0 251 520 A2 1/1988

(Continued)

OTHER PUBLICATIONS

Goknar, M. Kemal, Computer Mapping comes to behavioral health care, Behavioral Health Management, vol. 16, No. 1, pp. 17-20, 1996, dialog file #149, 0613413.*

(Continued)

*Primary Examiner*—Joseph Thomas
*Assistant Examiner*—Carolyn Bleck
(74) *Attorney, Agent, or Firm*—Myers Bigel Sibley & Sajovec

(57) ABSTRACT

A patient apparatus is configured to receive and analyze information regarding patient compliance with anticoagulation medication and self-test coagulation regimens related to anticoagulation therapy. In addition, a patient apparatus is configured to receive data from a patient, including physiological data, pathophysiological data, biological data, psychological data, neuropsychological data, and/or behavioral data. Utilizing the received patient data, a patient apparatus can modify a warfarin regimen using an algorithm contained within the apparatus. The apparatus can communicate the modified warfarin regimen to the patient and to third parties, such as remotely located healthcare providers. In addition, the apparatus can prompt a patient when to perform a self-test and can prompt a patient to seek immediate medical attention, or to directly contact medical help, when so warranted.

10 Claims, 21 Drawing Sheets

U.S. PATENT DOCUMENTS

| | | | |
|---|---|---|---|
| 5,822,715 A | 10/1998 | Worthington et al. | 702/19 |
| 5,840,020 A | 11/1998 | Heinonen et al. | 600/309 |
| 5,868,135 A | 2/1999 | Kaufman et al. | 600/300 |
| 5,868,669 A * | 2/1999 | Iliff | 600/300 |
| 5,907,291 A | 5/1999 | Chen et al. | 340/870.76 |
| 5,933,136 A | 8/1999 | Brown | 345/741 |
| 5,950,630 A * | 9/1999 | Portwood et al. | 128/897 |
| 5,954,641 A * | 9/1999 | Kehr et al. | 600/300 |
| 5,967,975 A * | 10/1999 | Ridgeway | 600/300 |
| 6,024,699 A * | 2/2000 | Surwit et al. | 600/300 |
| 6,080,106 A * | 6/2000 | Lloyd et al. | 600/300 |
| 6,085,752 A * | 7/2000 | Kehr et al. | 128/897 |
| 6,161,095 A * | 12/2000 | Brown | 705/2 |
| 6,171,237 B1 * | 1/2001 | Avitall et al. | 600/300 |
| 6,283,923 B1 * | 9/2001 | Finkelstein et al. | 600/532 |
| 6,302,844 B1 * | 10/2001 | Walker et al. | 600/300 |
| 6,364,834 B1 * | 4/2002 | Reuss et al. | 600/300 |
| 6,379,301 B1 * | 4/2002 | Worthington et al. | 600/309 |
| 6,514,200 B1 * | 2/2003 | Khouri | 600/300 |
| 6,524,239 B1 * | 2/2003 | Reed et al. | 600/300 |
| 6,525,670 B1 * | 2/2003 | Doi et al. | 340/870.16 |
| 6,607,485 B2 * | 8/2003 | Bardy | 600/300 |
| 6,834,203 B2 * | 12/2004 | Bardy | 600/518 |

FOREIGN PATENT DOCUMENTS

| | | |
|---|---|---|
| EP | 0 555 590 A2 | 8/1993 |
| JP | 2003030320 * | 1/2003 |
| WO | WO 96/27163 | 9/1996 |
| WO | WO 98/50873 | 11/1998 |
| WO | WO 99/03045 | 1/1999 |
| WO | WO 99/04043 | 1/1999 |

OTHER PUBLICATIONS

J.D. Piette, *Moving Diabetes Management From Clinic to Community: Development of a Prototype Based on Automated Voice Messaging*, The Diabetes Educator 23, No. 6, pp. 672-680 (1997).

J.E. Ansell et al; *Long-term Patient Self-management of Oral Anticoagulation*, Arch Intern Med 155: 2185-2189 (1995).

Puers, B. et al., *Patient Monitoring Systems*, VLSI and Computer Peripherals, Hamburg, Conf. No. 3, pp. 3-152-157 (May 8, 1989).

Benaroch, Lee M. et al., *A New Approach to Computer Directed Insulin Management Systems: DiaComp*, Proceedings of the Annual Symposium on Computer Based Medical Systems, Minneapolis, Symp. 2, pp. 89-96 (Jun. 26, 1989).

Mungall, Dennis, et al., *Software Applications in Anticoagulation, Managing Oral Anticoagulation Therapy: Clinical and Operational Guidelines*, Supp. 2, pp. 5A-2:1-5A-2:20 (Nov. 1999).

Abstract, Mungall, Dennis, *The Anticoagulation Clinic Without Walls: a Pilot study Comparing Internet Based Oral Anticoagulation Therapy with Anticoagulation Clinic care*, Anticoagulation Forum Meeting, Vancouver, Canada May 17, 1999 (1999).

Copy of International Search Report for PCT/US01/00789.

* cited by examiner

| Assessments | Breakfast | Lunch | Dinner | Late Night |
|---|---|---|---|---|
| | 18u Lente @Dinner Avg. BG 120 | 5u Semi-Lente @Breakfast Avg. BG 100 | 12u Lente @Breakfast Avg. BG 130 | 6u Semi-Lente @Dinner Avg. BG 115 |
| Adjustment | Enabled | Enabled | Enabled | Enabled |
| Increase if BG above | 100 | 130 | 140 | 140 |
| for Consec Days | 3 | 3 | 3 | 3 |
| Decrease if BG below | 50 | 55 | 55 | 55 |
| for Consec Days | 4 | 2 | 2 | 2 |
| Method | Percent ▷ | Units ▷ | Percent ▷ | Units ▷ |
| Amount | 10% | 1 | 5% | 1 |

APPARATUS AND METHODS FOR MONITORING AND MODIFYING ANTICOAGULATION THERAPY OF REMOTELY LOCATED PATIENTS

FIELD OF THE INVENTION

The present invention relates generally to data processing apparatus and methods and, more particularly, to medical monitoring apparatus and systems.

BACKGROUND OF THE INVENTION

Chronic disease management conventionally involves routinely monitoring patients who suffer from chronic disease to identify disease-related health problems before they become medically severe. Routine monitoring is also required in patients undergoing various forms of rehabilitation or primary prevention such as programs designed to promote healthy diet and exercise behavior. Disease management and prevention may also involve monitoring exercise and diet patterns of patients, as well as adherence to and adjustments of prescribed medicine. The management of chronic disease also often involves continuous treatment of a disease process with one or more medicines. Many of these medications have a relatively narrow therapeutic window; that is, there is a narrow range of medication dosages that provide optimal therapeutic effect without producing undesirable and potentially dangerous side effects. Other, often behavioral, factors such as illness, or changes in sleep, vitamins, diet, exercise, stress, menstrual cycles, etc. can impact the efficacy, absorption, dissipation, bioavailability and hence optimal dosing requirements of medication. Additionally, due to comorbid or co-occurring diseases or intercurrent illness, there are risks related to potential medication interactions that can also affect the efficacy dosing requirements of one or more of the medications used in treatment. Ideally, the effects of medication should be continuously monitored in order to insure that the patient is deriving maximal therapeutic benefit without suffering the effects of overmedication or from potentially dangerous interactions.

Most patient assessment of the efficacy of self-administered treatment programs such as medication regimens, rehabilitative recovery or primary prevention occurs in the offices of healthcare professionals. Unfortunately this is both time-consuming and expensive, and can only partially deal with issues related to timeliness and compliance. To overcome the disadvantages of requiring patients to visit a physician's office for assessment of their disease or condition, various health care organizations have implemented programs where case managers (i.e., persons with some level of medical training) telephone patients periodically to obtain patient data and to coordinate care. Unfortunately, with often hundreds of patients per case manager, personal contact with individual patients on a daily or even regular basis may be difficult. In addition, personal contact with individual patients on a regular basis may be somewhat expensive. Accordingly, case managers using conventional management techniques may not be able to monitor, adjust or promote a patient's medication dosage or other treatment regimen as often as desirable or necessary.

Another approach used in chronic disease management involves automated voice messaging (AVM) services, wherein patients receive regular telephone calls providing various educational and motivational messages from case managers. Exemplary messages may include reminding a patient of a scheduled physician visit. Some AVM services involve one-way communication, wherein a recorded message is delivered to a patient, but no information is obtained from the patient. As a result, the medical condition of a patient may not be available unless the patient is examined in-person by a physician.

AVM services involving two-way communications may allow patients to respond to AVM telephone queries via a touch tone telephone. Information received from patients may be reviewed by a case manager (CM). The CM then may identify which patients require callbacks for gathering more detailed information, discussing problems, or providing further information. Unfortunately, AVM services involving two-way communications may require some level of human intervention to identify patients with medically severe conditions that require immediate medical attention, such as a change in warfarin or insulin dosage. Chronic disease management via AVM has another drawback in that delays may occur between the identification of a patient with a medically severe condition and actual treatment of the condition.

In order to assist the physician and CM in following a patient with chronic disease, home monitoring devices have been developed and marketed that can collect physiologic data and report this data back to the physician. Examples of such devices include home blood glucose monitors, home blood pressure monitors, home peek-flow monitors for asthma, and home coagulation time monitors for patients undergoing anticoagulation therapy. While these systems can collect physiologic data at home, they do not provide direct guidance to the patient on need changes in chronic medication dosing. They also do not provide a convenient way for physicians to use the data generated to cost-effectively manage patients.

In addition to case managers, AVMs, and home diagnostic devices, several systems have been devised that collect disease-related data at home and transmit them to a central location where the data can be analyzed by a physician or other healthcare professionals. Such systems include DIABCARE (Roche Diagnostics), THE BUDDY SYSTEM, HEALTH HERO, and LIFECHART. Some of these systems directly interface with home physiologic monitors (e.g., DIABCARE and LIFECHART) as described above. However, all of these systems simply collect data from remotely-located patients and present the data in summary form. They do not attempt to help the physician or health care provider prioritize patients in need of attention, recommend actions to ameliorate the patient's condition, or give information back to the patient about what he or she should do in the event the a change in the therapy regimen in indicated.

One system that has attempted to automate disease management for insulin therapy in diabetes mellitus is the DIACARE® System, described in U.S. Pat. No. 4,731,726. Unfortunately, the DIACARE® System is narrowly focused on treating diabetic patients using insulin, and lacks many of the important features of a system that would be necessary for delivering a wide variety of interventions in a number of medical diseases or conditions such as anticoagulation therapy.

Warfarin and other anticoagulant therapies are indicated for conditions involving the increased likelihood of fibrin clot (thrombosis). These thromboses may increase the likelihood of stroke, myocardial infarctions or other cardiovascular events. Anticoagulant therapies interfere with or decrease the ability of the body to form a fibrin clot (thrombosis). Since under-medication can result in a thrombosis, and overmedication can result in potentially disastrous hemorrhagic complications, all of these therapies need to be very closely monitored. Examples of these therapies and the types of tests used to monitor them are shown in Table 1 below:

TABLE 1

Anticoagulation Therapies & Tests

| THERAPY | TEST |
| --- | --- |
| Warfarin and other vitamin K antagonists | Prothrombin (PT) |
| Heparin and similar glucosaminoglycans | Partial Thromboplastin Time (PTT) |
| | Activated Clotting Time (ACT) |
| | Specific heparin or low low molecular weight heparin assays |
| Direct thrombin inhibitors (e.g., hirutin, melagatgran) | Ecarin clotting time (ECT) |
| | Thrombin clotting time |
| | PT or PTT |

PT or other coagulation tests (listed in Table 1) and regular visits to the physician or clinic are needed to monitor anticoagulation therapy. Anticoagulation therapy is a highly individualized matter that should be monitored closely. Numerous factors, alone or in combination, including travel, changes in diet, environment, physical state and medication may influence response of a patient to anticoagulants. As such, anticoagulant dosage should be controlled by periodic determinations of prothrombin time (PT)/International Normalized Ratio (INR) or other suitable coagulation tests.

Coagulation tests and regular visits to the physician or clinic are typically required to effectively monitor anticoagulation therapy. Unfortunately, regular visits to a physician or clinic can be expensive and inconvenient. In addition, patients may be required to attend training prior to being allowed to self-administer medication and testing regimens. Such training may be too complex and/or cost-prohibitive for many patients.

SUMMARY OF THE INVENTION

In view of the above discussion, it is an object of the present invention to provide apparatus and methods that allow patients to remotely self-monitor disease therapy, such as anticoagulation or other therapies that can be optimized (i.e., deliver maximum therapeutic benefit in the most cost-effective way with minimal side effects and complications by close monitoring, and that can modify medication regimens without requiring a patient to visit a healthcare provider.

It is another object of the present invention to allow health care providers to quickly and easily monitor many patients and to automatically identify patients with medical conditions that are pertinent to ongoing therapies and to organize identified medical conditions by severity.

These and other objects of the present invention are provided by apparatus and methods that allow a patient to self-monitor disease therapy and other potentially important variables without requiring the patient to visit a healthcare provider. In this way, the effects of medication can be more frequently assessed. Both sub-therapeutic dosing (under-dosing of medication) and supra-therapeutic dosing (over-dosing of medication) can be detected and rapidly ameliorated. Both sub-therapeutic and supra-therapeutic dosing may be associated with acute morbidity and mortality. Sub-therapeutic dosing can allow the underlying disease process out of control, while supra-therapeutic dosing is often associated with intolerable side effects which in some cases can be dangerous or toxic. Furthermore, dosing requirements may change due to a variety of factors and cannot be assumed to remain constant.

According to one embodiment of the present invention, anticoagulation therapy is indicated for such diseases such as atrial fibrillation, deep venous thrombosis, and thrombosis secondary to prosthetic heart value replacement. Other medical diseases or conditions that can be managed using these methods include seizure disorders, attention deficit hyperactivity disorder, cancer therapies and palliative treatments, pain control, renal dysfunction, various forms of depression including manic depression, high blood pressure, asthma, physical rehabilitation following injury, surgery or stroke, cardiovascular conditioning in cardiac rehabilitation, primary prevention and wellness promotion in at-risk groups, can all be monitored and prescriptively controlled via a remote and preferably portable apparatus. Typically, disease therapy (also referred to as chronic disease management) includes a medication regimen (e.g., warfarin for anticoagulation therapy, lithium or DEPAKOTE® (Divalproex Sodium, Abbott Labs) medication for manic depression, DEPAKENE® (valproic acid, Abbott Labs) or TEGRETOL® (carbamazepine USP; Basel Pharmaceuticals) for seizure disorders, RITALIN® (methylphenidate hydrochloride USP; CIBA Pharmaceuticals) for attention deficit hyperactivity disorder, or G-CSF (granulocyte colony stimulating factor) or erythropoietin (a hormone manufactured primarily in the kidneys which stimulates red blood cell production) for cancer chemotherapy patients, L-dopa therapy in Parkinson's Disease, and test regimens for monitoring the efficacy or toxicity of the medication dosing regimen. In rehabilitation and wellness promotion the prescription may include exercises and assessment could involve measurement of physical conditioning, range of motion, strength, endurance, rigidity, fine motor control, tremors, and the like. These can be monitored remotely and algorithmically adjusted using prescribed software routines. Exemplary test regimens for diseases include prothrombin time (PT) test for anticoagulation, white blood cell count in cancer chemotherapy patients, potassium or bicarbonate in patients with renal failure, blood pressure in hypertension, heart rate recovering in physical conditioning, depression rating scores or neuropsychological test performance in depression, and pain rating scales in chronic pain, for example.

A patient apparatus (i.e., an apparatus utilized by a patient according to the present invention) is configured to receive and analyze information regarding patient compliance with medication and test regimens. A patient apparatus according to the present invention is also configured to receive information or data from a patient concerning supra-therapeutic and sub-therapeutic conditions, signs, symptoms or test results. This same patient apparatus may also be configured to obtain data from the patient on factors which could impact ongoing therapies, such as data concerning diet, exercise, sleep, stress, illness, vitamin and other medication usage. The type of data which the patient apparatus may receive from a patient could include, but would not be limited to, physiological, pathophysiological, biological, psychological, neuropsychological (cognitive performance), behavioral data and/or specific knowledge assessments. For example, a patient can provide information or data regarding mood status, reaction times, tasks measuring divided attention or concentration, or symptoms the patient may be experiencing, along with changes in diet, exercise, stress or other medications.

A patient apparatus according to the present invention can also actively promote compliance with the prescribed treatment regimens using alarm-based initiation of routines which prompt the patient to initiate self-assessment or self-treatment protocols. Software routines in the device or managed through the device and initiated via hardware alarms or communications from remotely connected devices, servers or services can engage the patient in creative ways and help maintain motivation, initiation and completion of self-care regimens.

Utilizing the received patient data, a patient apparatus can modify a medication regimen using an algorithm contained within the apparatus. The apparatus can communicate the modified medication regimen to the patient and to third parties, such as remotely located healthcare providers. The apparatus can prompt a patient when to perform various types of self-assessments and home self-testing to provide data, directed towards monitoring the efficacy of a medication. In addition, the apparatus can prompt a patient to seek medical attention when so warranted. A patient apparatus according to the present invention can also automatically communicate patient information to a healthcare provider (or other third party) if the patient apparatus determines that symptoms that a patient is experiencing are above a severity threshold level.

According to another embodiment of the present invention, a patient apparatus for monitoring and modifying disease therapy can communicate directly with a remotely located data processing system that is configured to analyze data transmitted from the patient apparatus substantially simultaneously with the transmission thereof to identify emergency medical conditions requiring immediate medical attention. In response to identifying an emergency medical condition, treatment information may be automatically communicated to the respective patient apparatus while communications are still established.

The present invention provides a generic tool for automating the management of therapies for many chronic diseases, medical conditions or primary preventative interventions. A patient apparatus according to the present invention is ideally suited for conditions in which medication or other self-administered treatments are systematically administered and whose effects should be closely monitored, in order to maximize therapeutic benefit and minimize the risks of overmedication or other over-treatment. However, it can also significantly improve the cost effectiveness of delivering and assessing educational, rehabilitative and primary prevention programs in the patient's home environment. This invention involves the establishment of a remote electronic link between patient and caregiver, wherein the patient provides various types of assessment data and receives individualized interventions. Most patient interventions provided by this system will can be algorithmically programmed to automatically recommend individualized medication or other treatment changes in real time, or following communication with a remote computer system which is configured by the healthcare provider for patients. Besides providing access to these automated adjustment parameters, the healthcare provider's electronic interface contains powerful tools for assessing patient progress, prioritizing problems and screening for emergency conditions. The present invention is well suited for self-care regimens involving medications with a narrow therapeutic window, and will be thoroughly and primarily described throughout this disclosure with respect to the control of patients undergoing anticoagulation therapy. However, the potential applications for this system are broader and can apply to the control of other medications and/or interventions used in the prevention or treatment of other diseases.

BRIEF DESCRIPTION OF THE DRAWINGS

FIGS. 10A–10C illustrate exemplary user interfaces for facilitating communications with a remotely located patient.

FIG. 11 illustrates an exemplary user interface for adjusting a medicine dosage algorithm stored within a patient's PPM.

FIG. 14 illustrates an exemplary user interface for removing an identified medical condition from an active list.

DETAILED DESCRIPTION OF THE INVENTION

Figure 1:
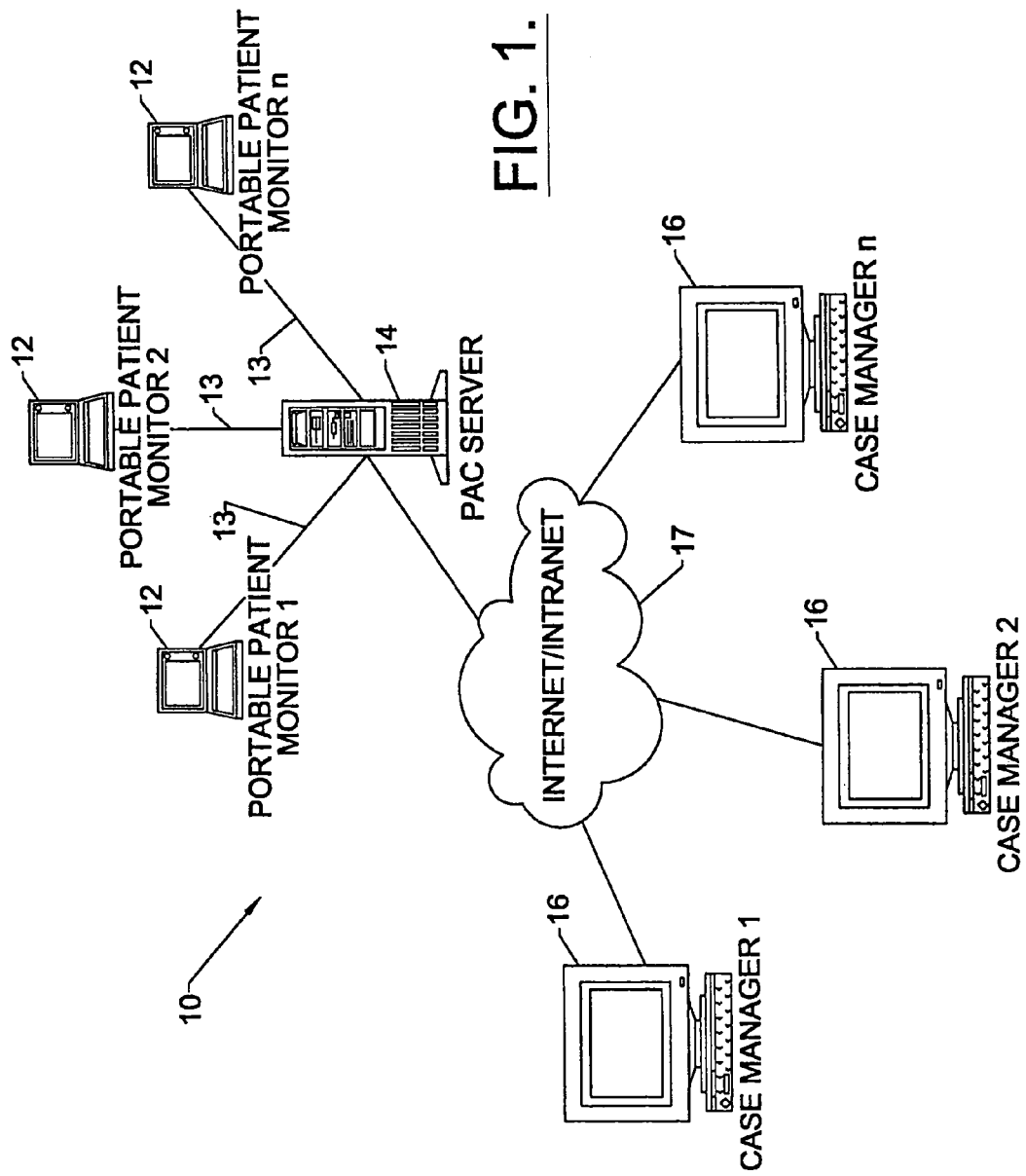
FIG. 1 schematically illustrates a system for monitoring, diagnosing and treating medical conditions of a plurality of remotely located patients according to an embodiment of the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. The present invention will now be described more fully hereinafter with reference to the accompanying drawings, in which preferred embodiments of the invention are shown. Like numbers refer to like elements throughout.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects. Furthermore, the present invention may take the form of a computer program product on a computer-readable storage medium having computer-readable program code means embodied in the medium. Any suitable computer medium may be utilized including hard disks, CD-ROMs, optical storage devices, or magnetic storage devices.

The present invention is described below with reference to flowchart illustrations of methods, apparatus (systems) and computer program products according to embodiments of the invention. It will be understood that each block of the flowchart illustrations, and combinations of blocks in the flowchart illustrations, can be implemented by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

These computer program instructions may also be stored in a computer-usable memory that can direct a computer or other programmable data processing apparatus to function in a particular manner, such that the instructions stored in the computer-usable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Accordingly, blocks of the flowchart illustrations support combinations of means for performing the specified functions, combinations of steps for performing the specified functions and program instruction means for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer instructions.

Computer program for implementing the present invention may be written in various object-oriented programming languages, such as Delphi and Java®. However, it is understood that other object oriented programming languages, such as C++ and Smalltalk, as well as conventional programming languages, such as FORTRAN or COBOL, could be utilized without departing from the spirit and intent of the present invention.

System Overview

Referring now to FIG. 1, a system 10 for monitoring, diagnosing, and treating medical conditions of remotely located patients with various chronic illnesses, according to the present invention, is schematically illustrated. A plurality of remote or preferably portable patient monitors (PPMs) 12 are configured to establish communications directly with a central data processing system referred to as a Physicians Access Center server (hereinafter "PAC server") 14 via communications links 13. It is noted that a majority of the functionality provided by a PPM as described herein for many disease applications can be achieved using remote data terminals or internet browsers, which are not necessarily portable, but which can provide personal healthcare advice via connection to a properly configured database server system that supports the features of a PPM described below.

A plurality of case manager clients (CMCs) 16 are configured to establish client-server communications with the PAC server 14 via a computer network 17, such as the Internet or an Intranet. The term "CMC" can be considered as a synonym for professional or paraprofessional healthcare providers. It is understood that a CMC or PAC server or other apparatus configured to execute program code embodied within computer usable media, operates as means for performing the various functions and carries out the methods of the various operations of the present invention. It is also understood that the present invention may be used with various client-server communications protocols, and is not limited to specific protocols such as TCP/IP protocol.

Each of these components will be described in detail below. The present invention will be described throughout this disclosure with respect to the control of warfarin therapy for patients undergoing anticoagulation therapy. However, it is to be understood that the present invention may be utilized with a wide variety of medical therapies including, but not limited to, antiseizure therapy, cancer chemotherapy, renal failure therapy, congestive heart failure therapy, asthma therapy, high blood pressure therapy, attention deficit disorder therapy, depression therapy, and therapies for other chronic diseases and conditions.

For example a PPM may collect and use patient data to adjust medication dosage for respiratory therapy and anticoagulation therapy based on predefined physician prescriptions. The term "prescription" may include physician-prescribed algorithms for calculating medicine dosages, dosages calculated from algorithms, and fixed and contingent self-monitoring schedules for patients. An exemplary physician-prescribed medication algorithm is described in *Guidelines for the Diagnosis and Management of Asthma; Expert Panel Report Two*; National Institutes of Health; Heart and Lung Institute; Publication No.: 97-4051, April 1997, which is incorporated herein by reference in its entirety. Another exemplary physician-prescribed medication algorithm is described in *Long-term Patient Self-management of Oral Anticoagulation*; Jack E. Ansell et al.; Arch Intern Med. 1995; Vol. 155; pp. 2185–2189; which is incorporated herein by reference in its entirety.

A PPM may incorporate physician-prescribed algorithms for calculating medicine dosages for various chronic illnesses. Alternatively, a PAC server may implement a medication dosage algorithm for anticoagulation therapy, based on values communicated to the PAC server by a PPM, and communicate results directly to the patient. PAC server implemented dosage algorithms may be a logical alternative to having medication dosage algorithms stored within PPMs when medication dosage changes are infrequent.

Remote or Portable Patient Monitors (PPM)

A PPM (12 in FIG. 1) serves as primary means for collecting data from a patient and as means for case managers to interface with a patient. Exemplary features of a PPM for use in accordance with the present invention are summarized below in Table 2.

TABLE 2

Small and portable so patient can carry around.
Data processing capabilities and built-in modem or attachable external modem.
Collects data from blood, breath or bodily fluids or other functions.
Collects patient supplied data on health status, compliance with a medical treatment or management regimen, and psychological data.
Allows two-way communication with PAC server.
Analyzes patient data collected and delivers pre-recorded or calculated responses and/or medication dosage recommendations based on physician instructions loaded in PPM.
Downloads patient data to PAC server at specified time intervals or in real time.
Receives messages, updates to physician instructions and prescription dosage parameters, dosage algorithms, fixed or contingent self-monitoring schedules, words of encouragement or other feedback from PAC server.

Patient data collected via a PPM may include physiologic or biologic data and behavioral data (e.g., assessments related to diet, exercise, stress, mental status or the presence of intercurrent illness). A PPM may also monitor patient medication intake (e.g., warfarin dosage). A PPM, depending on the chronic illness of the patient, may contain software specifically designed for a particular patient's illness. For example; a PPM for an anticoagulation therapy patient may contain physician-prescribed warfarin dosage algorithms. It is understood that other medications, well known by those of skill in the art, may be utilized in anticoagulation therapy in addition to, or in lieu of, warfarin.

A PPM designed for a patient can store various data along with other relevant self-monitoring patient data. Blood from a pricked finger may be read on a chemically treated strip via the PPM. Automated warfarin adjustment algorithms with physician-prescribed parameters can be stored within each patient's PPM for real-time analysis and adjustment of a patient's warfarin dosage. The PPM may be configured to make automatic adjustments to a patient's self-monitoring and treatment regimen based on patient-entered data as will be described below. A PPM may also contain a database to help patients evaluate the effects of new medications on their target disease or to provide other disease-specific information to patients.

With respect to medications, the term "regimen" is intended to be synonymous with a schedule for taking medication. However, it is understood that some medications are taken in different doses on different days (or other time periods). Thus, the term "regimen" also refers to dosage amounts of a medication taken according to a particular schedule. Thus, the term "modifying a medication regimen" may include changing a schedule for taking a medication and/or changing a dosage amount of a medication. With respect to tests for monitoring the efficacy of medication in disease therapy, the term "regimen" is intended to be synonymous with a schedule for taking a test. Thus, the term "modifying a test regimen" may include changing a schedule for administering a test.

Patients are responsible for recording data within their PPMs and transmitting the data to a PAC server on a regular basis. Preferably, transmission of data to a PAC server is highly automated and substantially "hands-off" for a patient. A patient preferably can plug a PPM into a standard telephone jack and, with the press of a button, establish communications with a PAC server. Each PPM may have the ability to prompt patients when data transmissions are required, and to initiate and complete data transmissions using an alarm-driven timer.

Preferably, each PPM contains a user interface for displaying text, graphics, prompts and various other information. A PPM user interface serves as the primary means of communication between the PAC server and the patient. A PPM may also be configured to notify patients of transmission schedules to the PAC server; to notify patients having emergency medical conditions to promptly seek medical attention; and to provide motivational feedback to patients based upon past performance (e.g., reward patients for keeping on schedule with data recordings and transmissions of data to a PAC server).

Figure 2:
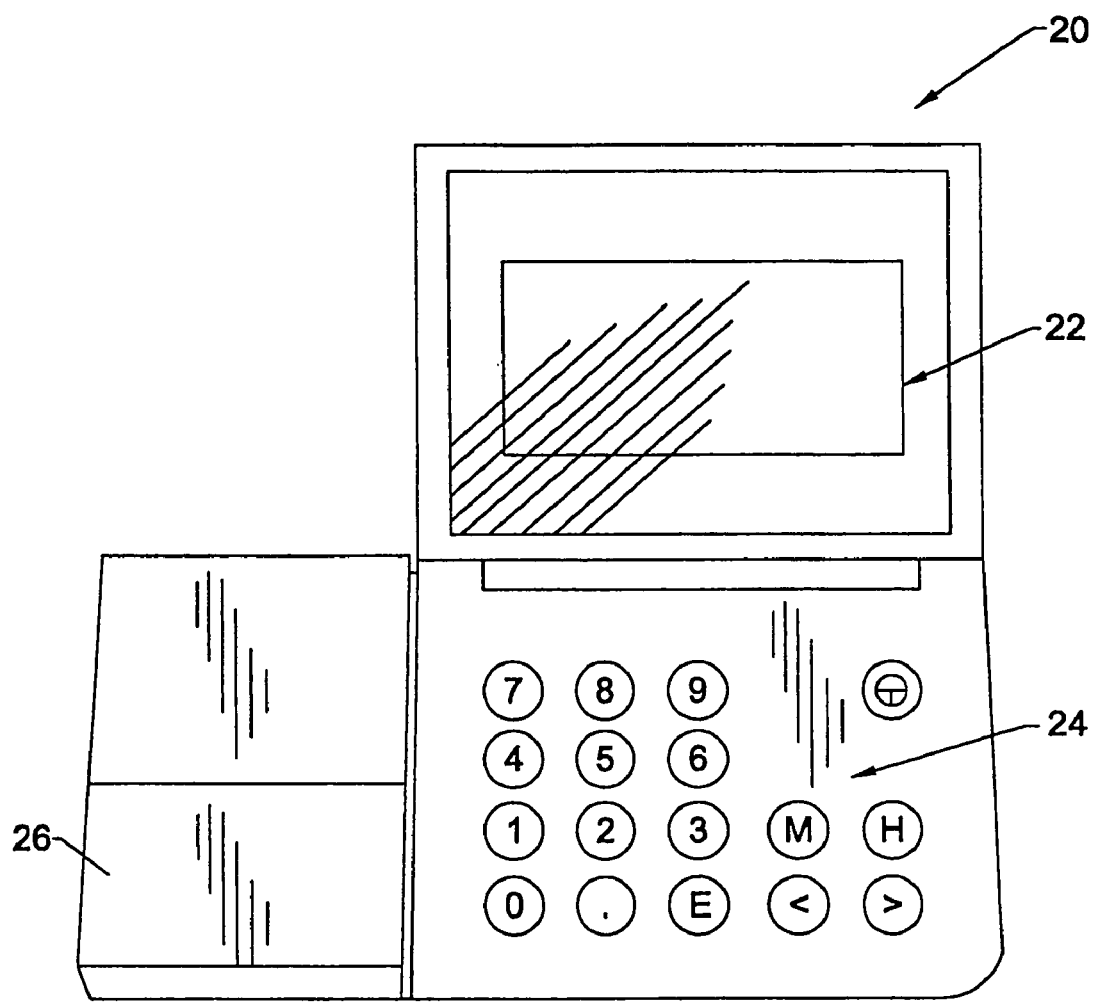
FIG. 2 illustrates an exemplary portable patient monitor (PPM).

Referring now to FIG. 2, an exemplary PPM 20 is illustrated. The illustrated PPM 20 includes a display 22 and a keyboard 24. The PPM 20 also preferably includes the following which are not shown: internal, non-volatile data storage, internally stored medication monitoring software, and a data processor for performing various functions and for communicating with a PAC server. Internal software (program code) may query a patient for various information via display 22. Preferably, the PPM internal software is menu-driven for ease-of-use by patients. Preferably, the menus are written in various languages including a children's version incorporating game-like features.

Preferably, all data entered within a PPM 20 is stored with date and time information and can be alarm initiated (i.e., a patient or PPM can be prompted to perform a task or function). Preferably, the PPM internal software analyzes the entered data and continuously informs the patient of his/her prescribed medication dose. The PPM internal software can calculate adjustments for a patient's medication dosage according to a physician's prescription as applied to the data entered into the PPM by the patient.

The internal software of a PPM can be configurable by a case manager via a PAC server. A case manager can make adjustments to a patient's medication dose calculations, to a patient's dosage algorithm, and to a patient's fixed or contingent self-monitoring schedules. These adjustments can be made automatically within a PPM during routine data transfer to a PAC server. In addition to providing disease therapy management, a PPM can be used to remind patients to schedule appointments for important examinations.

Preferably, a PPM contains a database of medication interaction information and is configured to allow a patient to query the database for information related to the patient's use of multiple medications. A PPM may be configured to communicate with an external database containing medication interaction information, as well. For example, a patient may query a database located within a PAC server when communications are established between the PPM and the PAC server. A PPM may also be configured to allow a patient to establish communications with other external databases, such as those residing in various legacy systems.

Other features of a PPM which are not illustrated, but which may be included, are PCMCIA slots for connecting a PPM to various peripheral devices; RJ11 connections to land line telephone systems; and infrared ports for communications with peripheral devices. Additional PPM features for diabetes patients are disclosed in U.S. Pat. No. 4,731,726 which is incorporated herein by reference in its entirety.

PPMs, according to the present invention, are not limited to land line telephone communications with a PAC server. PPMs may communicate with a PAC server using various communications technologies, without limitation. For example, a PPM may incorporate wireless communications technology for communicating with a PAC server. A PPM may also incorporate direct satellite communications technology for communicating with a PAC server.

Physician Access Center Server

Data entered into a PPM (12 of FIG. 1) by a patient is transferred to a central data processing system 14 (referred to hereinafter as a PAC server) via a telephone and modem. It is understood that a PAC server 14 may be one or more data processing devices arranged in a network. Preferably, a direct communications connection is established between a PPM 12 and a PAC server 14. Alternatively, an indirect communications connection may be established between a PPM 12 and the PAC server 14 via the Internet or other network. A communications server is preferably utilized to handle inbound and outbound communications between a PPM 12 and the PAC server 14, as would be understood by those skilled in the art of client-server communications. The term PAC server, as used herein, includes databases for storing and manipulating patient data as well as other server functions including, but not limited to web servers, application servers, e-mail servers, fax servers, AVM servers, and the like. A particularly preferred PAC server utilizes an Intel based processor running Windows NT Server 4.0 as its operating system. Preferably, a PAC server 14 is configured to handle more than 250,000 patients with at least 500 concurrent client connections. However, a PAC server 14 may be implemented using other processors and via other computing devices, including, but not limited to, mainframe computing systems and mini-computers.

A PAC server 14 analyzes and stores data transmitted from each patient PPM 12. This data is made available to authorized case managers who can access the data via a CCM 16 in TCP communication with a PAC server 14 via the Internet. In particular, a PAC server 14 identifies and prioritizes patient medical problems using the data transmitted from the patient PPMs 12. This allows case managers to focus their attention first on patients with significant medical problems.

Preferably, a PAC server 14 performs real-time analysis on data as it is being transmitted from a PPM to identify medical emergency situations that require immediate attention. If such a medical emergency is identified, a patient can be immediately notified via communications from a PAC server 14 to a PPM 12, without the intervention of a case manager. Alternatively, a case manager can be notified and the patient contacted directly via phone, e-mail, fax, or other modes of communication.

A PAC server 14 performs various other functions including allowing case managers to change the treatment program for patients, such as medication dosage, when a patient downloads data to a PAC server 14. In addition, a PAC server may include a "tickler system" for reminding case managers to verify that communications with patients have occurred and for verifying that medical conditions requiring medical attention have been resolved. A PAC server may also be configured to track patient medication supply usage automatically (e.g., warfarin, lancets, and syringes) and this information may be used to provide just-in-time delivery of replacement medications and supplies to a patient. A PAC server may be configured to communicate with manufacturers and distributors of medical supplies utilized by patients. By monitoring patient usage of supplies, orders can be placed with manufacturers and distributors directly via a PAC server such that medical supplies can be delivered to patients.

A separate warehouse database may be added to a PAC server 14 to support complex analysis of patient data, and may also be used to review prescriptive changes made to a patient's medical regimens and medication dosages.

Case Manager Clients

As illustrated in FIG. 1, case managers access a PAC server 14 via a case manager client (CMC) 16 connected to the same network. The CMC 16 preferably communicates with a PAC server 14 using TCP/IP protocol over an Internet connection between the CMC and the PAC server. Data encryption may be utilized and other security methods may be implemented to transfer information between a PPM and PAC server and between a CMC and the PAC server or a PPM.

Exemplary devices which may serve as CMCs 16 for purposes of the present invention may include, but are not limited to, desktop computers and portable computing devices, such as personal digital assistants (PDAs). A CMC 16 preferably includes a central processing unit, a display, a pointing device, a keyboard, access to persistent data storage, and an Internet connection for connecting to the Internet 17. An Internet connection may be made via a modem connected to traditional phone lines, an ISDN link, a T1 link, a T3 link, via cable television, via an ethernet network, and the like. An Internet connection may be made via a third party, such as an "Internet Service Provider" ("ISP").

An Internet connection may be made either by a direct connection of a CMC to the Internet or indirectly via another device connected to the Internet. In the latter case, a CMC is typically connected to this device via a local or wide area network (LAN or WAN). Preferably, data transfer rates between a CMC and a PAC server are equal to, or greater than, fourteen thousand four hundred baud (14,400 baud). However, lower data transfer rates may be utilized.

Preferably, a CMC 16 has an Intel® 80486 processor (or equivalent) with at least eight megabytes (8 MB) of RAM, and at least five megabytes (5 MB) of persistent computer storage for caching. Even more preferable is an Intel® Pentium® processor (or equivalent). However, it is to be understood that various processors may be utilized to carry out the present invention without being limited to those enumerated herein. Although a color display is preferable, a black and white display or standard broadcast or cable television monitor may be used. A CMC 16, if an IBM®, or IBM-compatible personal computer, preferably utilizes either a WINDOWS®3.1, WINDOWS 95®, WINDOWS NT®, UNIX®, or OS/2® operating system. However, it is to be understood that a terminal not having computational capability, such as an IBM® 3270 terminal or a network computer (NC), or having limited computational capability, such as a network PC (Net PC) may be utilized in accordance with an embodiment of the present invention for accessing the Internet in a client capacity.

Herein, the term "Internet" shall incorporate the term "computer network" and "communications network" such as an "Intranet", and any references to accessing the Internet shall be understood to mean accessing a hardwired computer network as well. Herein, the terms "computer network" and "communications network" shall incorporate publicly accessible computer networks and private computer networks, and shall be understood to support modem dial-up connections.

A case manager accesses a PAC server 14 via a CMC 16 to review the medical conditions of multiple patients. Case managers preferably are able to review, via information downloaded from a PAC server 14, all patient activity and data for their assigned patients including data transmission history, symptom reports, prescription review, analysis and adjustment. A CMC 16 allows a case manager to review patient data in various formats, including a hierarchical, problem-oriented format wherein patients with medical conditions requiring immediate attention are presented foremost. A CMC 16 may also allow a case manager to add, edit, and delete certain patient data stored in a PAC server 14. A CMC 16 also can interface directly with each PPM 12 to provide a patient with information and to modify illness-specific software contained therein. For example, a warfarin or other anticoagulation dosage algorithm contained within the internal software of a particular patient's PPM can be modified remotely by a case manager via a CMC 16.

System Security

Access to a system for monitoring, diagnosing, and treating medical conditions of remotely located patients with various chronic illnesses, according to the present invention, may be controlled using logon security which provides case managers and other users with certain circumscribed privileges to examine and/or edit data. These rights can limit certain users ability to examine confidential clinical health data, and may also be employed to limit the ability to edit any clinical data or make changes to specific fields in a patient's medication dosages or dosage adjustment algorithm. Similar access control may be applied to the data, at various levels, which define patients' medical conditions and their associated priorities and pre-emptive relationships.

Flexible configuration and associated security may be an element of a system for monitoring, diagnosing, and treating medical conditions of remotely located patients, according to the present invention, that permeates many of the subsystems. Default values and classifications for many values may be provided at the system level. Default values may be modified in a hierarchical manner, and may be controlled in part by access rights of a user, to a permit uniqueness at various levels.

Operations

Figure 3:
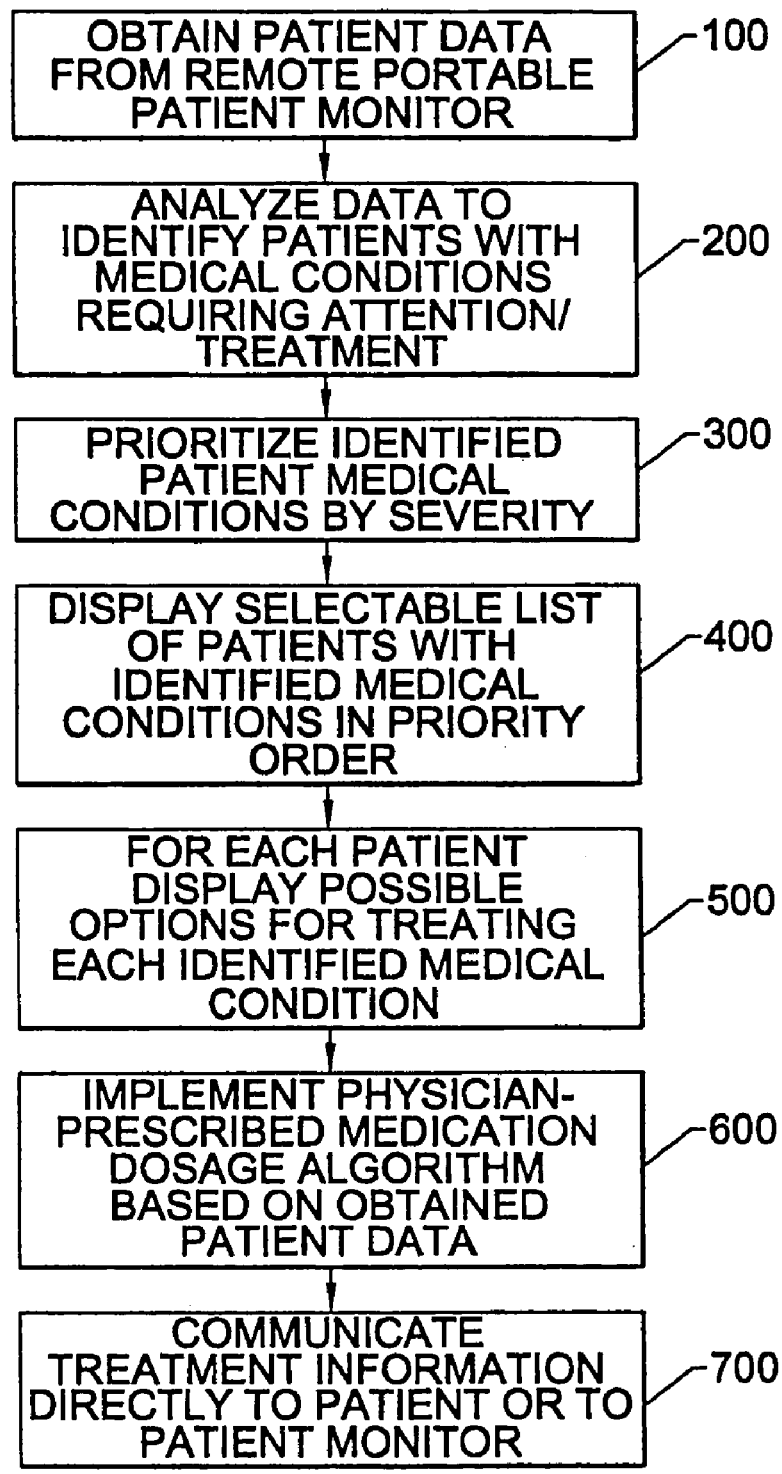
FIG. 3 schematically illustrates operations for monitoring, diagnosing and treating medical conditions of a plurality of remotely located patients according to the present invention.

Referring now to FIG. 3, operations for monitoring, identifying, prioritizing and treating medical conditions of patients with chronic illnesses, according to the present invention, are schematically illustrated. Patient data are obtained by a PAC server from a PPM (Block 100). A PAC server analyzes the obtained data to identify patients with medical conditions requiring treatment or some type of medical attention (Block 200). A PAC server prioritizes the identified patient conditions according to medical severity (Block 300). A PAC server displays to a case manager (or other user), via a client in communication with the PAC server, a selectable list of patients with identified medical conditions arranged in priority order (Block 400). A PAC server provides to a case manager, via a client, options for treating each identified medical condition (Block 500). Physician-prescribed medication dosage algorithms may be implemented based on patient data obtained from a PPM (Block 600). Treatment information may be communicated directly to a patient or to a patient's PPM by a case manager via a client in communication with a central data processing system (Block 700). The operations set forth in FIG. 3 are described in detail below.

Obtaining Data from PPM

Figure 4:
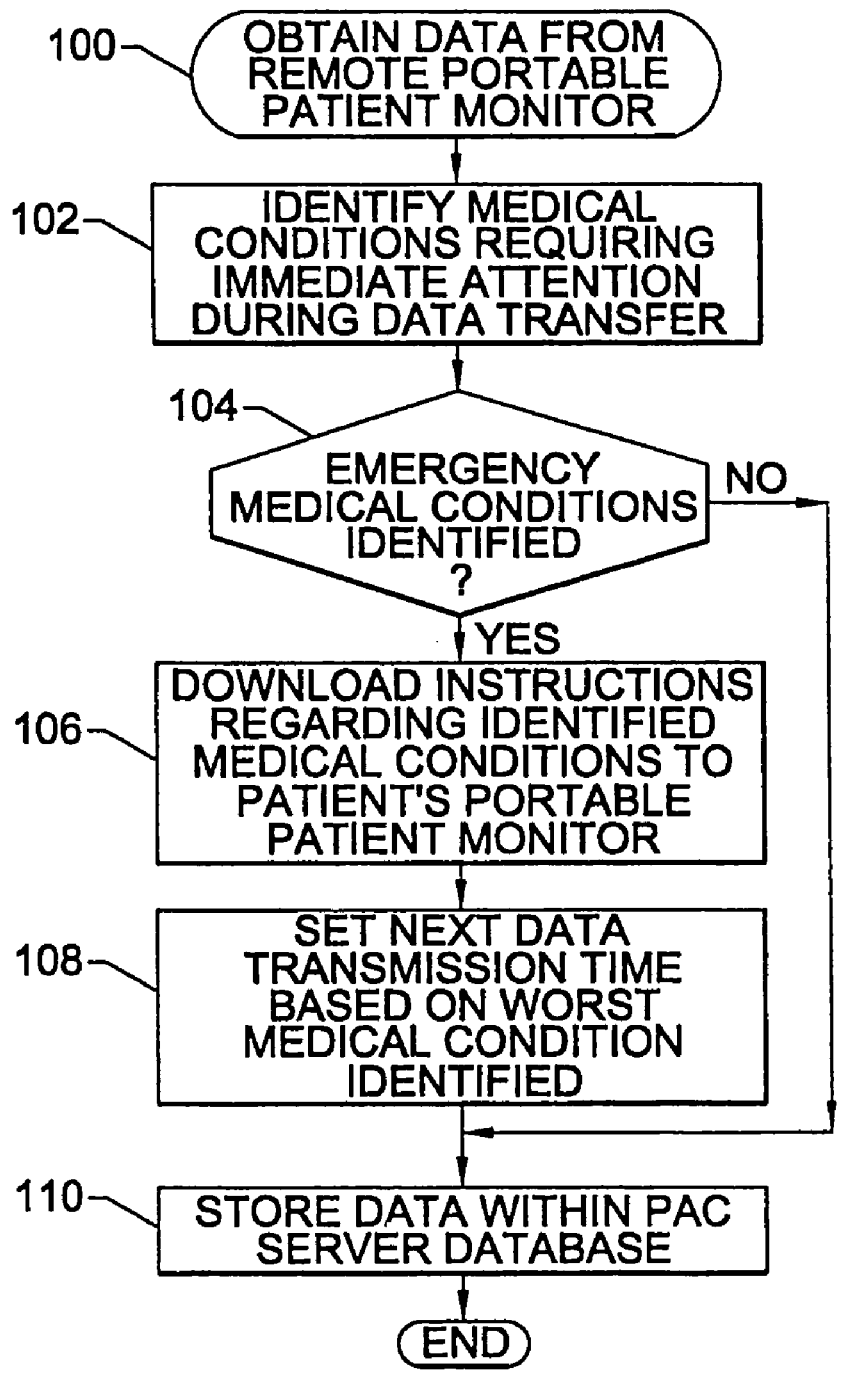
FIG. 4 schematically illustrates operations for obtaining data from a remotely located patient monitoring device.

In a preferred embodiment, when a PAC server obtains patient data from a PPM (Block 100), operations schematically illustrated in FIG. 4 may be performed. Preferably, data transmitted to a PAC server is analyzed substantially simultaneously with transmission of the data for the purposes of identifying "emergency" medical conditions requiring immediate medical attention (Block 102). Preferably, this analysis is performed while communications are still established between a PAC server and a PPM transmitting the data. If emergency medical conditions are not identified (Block 104), data obtained from a PPM is stored within a PAC server database for later analysis and retrieval (Block 110).

If emergency medical conditions are identified (Block 104), instructions are downloaded to the PPM regarding what actions should be taken by the patient (Block 106). For example, the patient may be instructed to immediately take a specific medication or to immediately seek medical attention. If a medication dosage algorithm is stored in a PAC server, the PAC server may communicate a new medication dose to the PPM, or to the patient via telephone, AVM, e-mail, facsimile transmission, and the like. In addition, changes may also be made to medicine dosage algorithms stored within a PPM or within the PAC server, such that a patient's next dose of medicine is changed in response to the identified emergency medical condition. Furthermore, changes may also be made to a patient's fixed or contingent self-monitoring schedules. The next scheduled time for data transmission from the PPM to the PAC server may be set, based on an identified medical condition's severity, such that higher condition severities result in more frequently scheduled transmissions (Block 108). For example, PPMs for patients with asthma may be reprogrammed to transmit every 12 hours, while PPMs for patients with high blood pressure may be adjusted to transmit every 3 days, while patients with no identified conditions may transmit on a routine schedule such as every week. The data obtained from a PPM is then stored within a PAC server database for later analysis and retrieval (Block 110).

Figure 5:
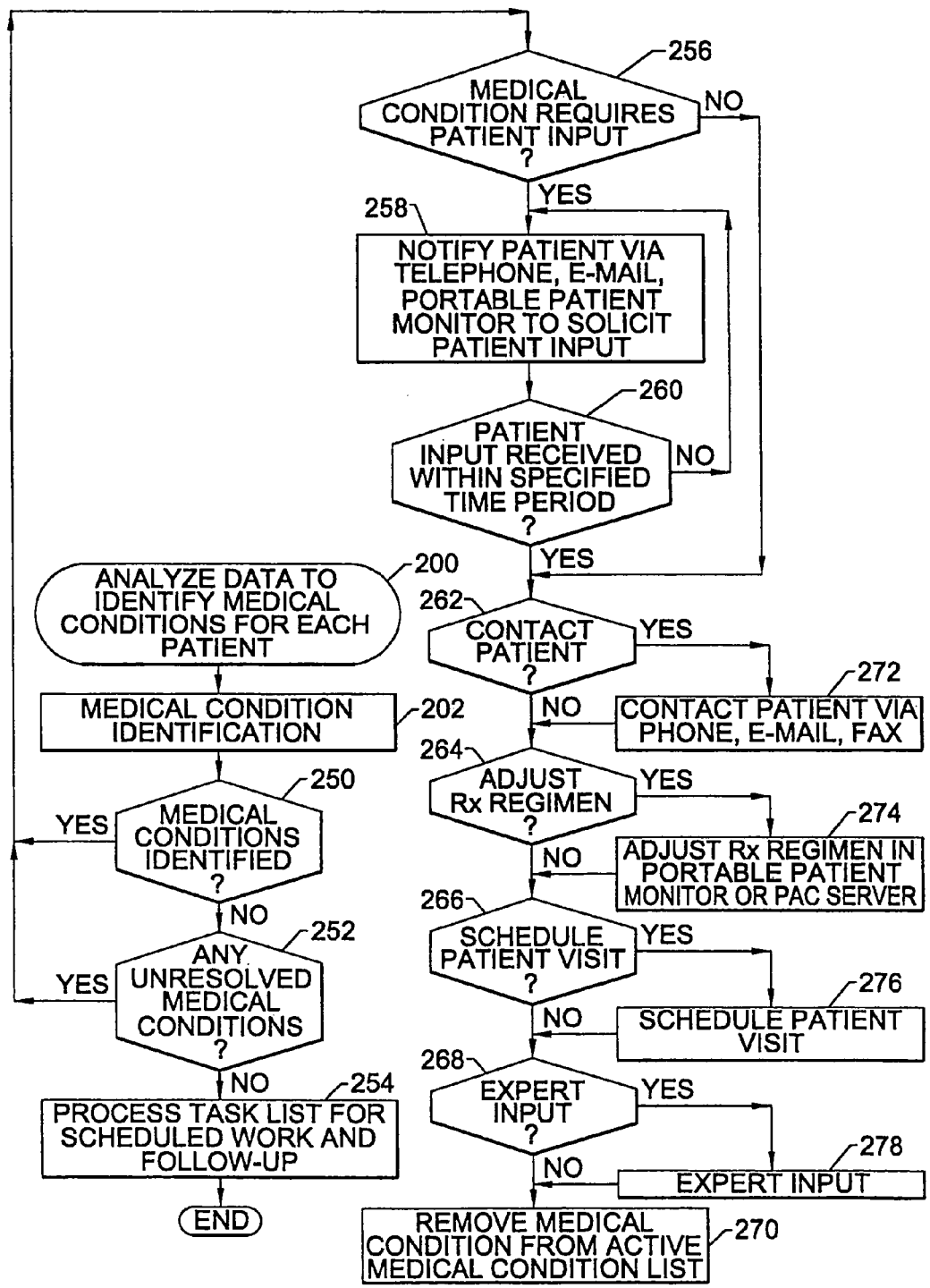
FIG. 5 schematically illustrates operations for analyzing data to identify medical conditions of a remotely located patient.
Figure 6:
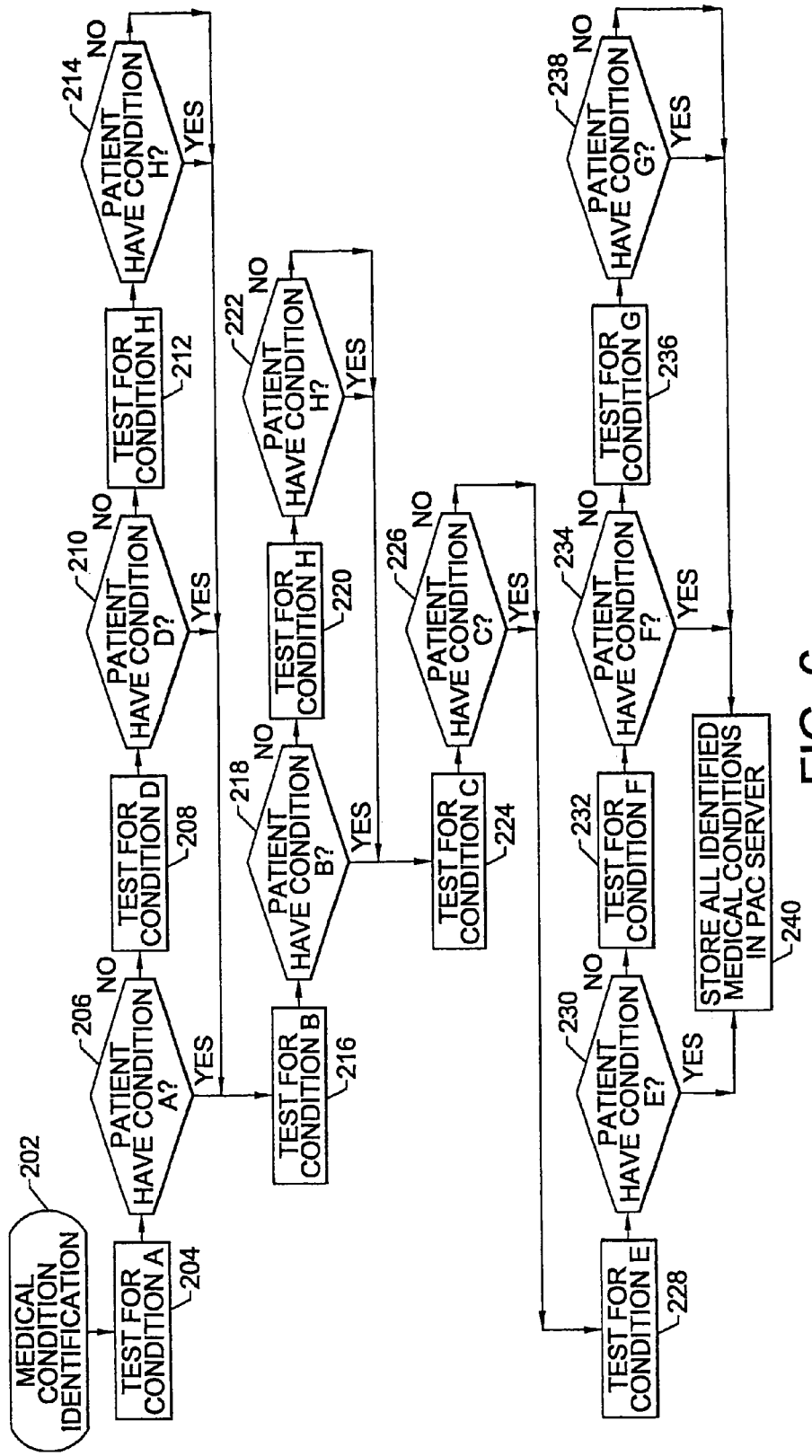
FIG. 6 schematically illustrates operations for identifying medical conditions according to aspects of the present invention.

Analyzing Patient Data to Identify Patients with Medical Conditions Requiring Medical Attention or Treatment Referring now to FIG. 5, preferred operations for analyzing patient data transmitted from a PPM to a PAC server to identify medical conditions requiring medical attention or treatment are schematically illustrated. Initially, operations for identifying medical conditions from transmitted data (Block 202) are performed. Exemplary operations represented by Block 202 are schematically illustrated in FIG. 6, and are discussed below.

Still referring to FIG. 5, if medical conditions requiring attention are not identified from data transmitted from a PPM (Block 250), a determination is made whether there are any unresolved medical conditions for the patient requiring attention or treatment (Block 252). If there are no unresolved medical conditions, case managers may provide patients with positive feedback to reinforce their self-monitoring practices and encourage continued compliance with the treatment regimen(s) (Block 254). Additionally, patients with chronic diseases must have regularly scheduled reviews and assessments, with the latter performed predominantly in the clinic. Periodic comprehensive reviews of the patients can be performed and may utilize all available inputs, including the most recent month's PPM data. These periodic assessments may be flexibly scheduled depending upon the disease and/or disease state of individual patients. These reviews provide a structured means by which the case manager may work to optimize care for patients who otherwise are not specifically identified as having medical conditions that require treatment, but who nonetheless can benefit by feedback and further optimization of medication doses, algorithmic methods for adjusting doses, self-monitoring schedule and by coordinating medical assessments and procedure conducted by other medical specialists.

If medical conditions are identified (Block 250) from transmitted data from a PPM, or if there are unresolved medical conditions for the patient (Block 252), a determination is made whether a medical condition requires additional patient input (Block 256). If patient input is required, the patient is notified by various methods, such as via telephone, e-mail, AVM, facsimile transmission, or via the patient's PPM (Block 258). Preferably, the present invention includes a "tickler" system for monitoring whether a patient provides required input within a specified time period (Block 260). If a patient does not provide required input within a specified time period, the present invention may prompt a case manager to re-notify a patient of required input (Block 258).

If input from a patient is not required (Block 256) or if patient input has been received (Block 260), a case manager is provided with various options for resolving one or more medical conditions. A case manager may be presented with an option to contact a patient (Block 262). If a case manager decides to contact a patient, the present invention facilitates communication via telephone, e-mail, AVM and facsimile transmission (Block 272). A case manager may be presented with an option to adjust a medicine dosage algorithm, a patient's dosage, or a patient's fixed or contingent self-monitoring schedule, either within a patient's PPM or the PAC server (Block 264). If a case manager decides to adjust a medicine dosage algorithm within a patient's PPM, the present invention facilitates this modification though a PAC server the next time communications are established between the PAC server and the patient's PPM (Block 274). A patient may be prompted to establish communications between his/her PPM and a PAC server to receive modifications made by a case manager. Alternatively, if a medicine dosage algorithm resides within a PAC server, a case manager can instruct the PAC server to adjust medicine dosage and transmit this information to the patient.

In addition, a case manager may be presented with an option to schedule a patient for a visit with a health care provider (Block 266) or with an option to seek expert medical input (Block 268). If these options are selected, the present invention facilitates scheduling a patient to visit a health care provider (Block 276) or obtaining input from a medical expert (Block 278). A case manager may decide that no action is required for a particular medical condition and may remove an identified medical condition from an active medical condition list for a particular patient after reviewing available data (Block 270).

Referring now to FIG. 6, exemplary operations performed by a PAC server for identifying medical conditions requiring medical attention or treatment are schematically illustrated. Preferably, these operations are performed by a PAC server immediately after transmission of data from a PPM to the PAC server. For any given chronic disease, there may be relationships between medical conditions that a patient may have. For example, a patient afflicted with thrombosis may exhibit two medical conditions having differing degrees of medical severity. One medical condition may have a high degree of medical severity requiring immediate attention. The other medical condition may have a much lower priority and may not require immediate medical attention. When multiple medical conditions are identified, two or more of these conditions for a given patient may represent problems of a similar type which differ only in severity (as defined by the system implementation). Conditions of lesser severity of the same type may be ignored (if identified) or may not be identified in the first place, if a condition of the same type at a higher priority has already been identified. It is presumed that identification and treatment of the most severe condition identified will obviate the needs to identify or treatment less severe conditions of the same type. Two methods are presented for achieving this aim below.

The present invention facilitates identifying and addressing medical conditions having the highest degree of medical severity first by organizing possible medical conditions for a given chronic disease into various classifications and by prioritizing medical conditions within each classification. Classification and prioritization within classes are illustrated below with respect to Table 3.

TABLE 3

| CLASS | MEDICAL CONDITION | PRIORITY | SUB_PRIORITY |
|---|---|---|---|
| 1 | A | 1 | A |
| 1 | A | 1 | B |
| 1 | A | 1 | D |
| 1 | A | 1 | L |
| 1 | A | 1 | Q |
| 1 | B | 2 | A |
| 1 | B | 2 | D |
| 1 | B | 2 | F |
| 1 | B | 2 | M |
| 1 | B | 2 | Q |
| 1 | B | 2 | Z |
| 1 | C | 3 | A |
| 1 | C | 3 | B |
| 1 | C | 3 | S |
| 1 | C | 3 | U |
| 2 | D | 1 | A |
| 2 | D | 1 | B |
| 2 | D | 1 | C |
| 2 | D | 1 | F |
| 2 | E | 2 | A |
| 2 | E | 2 | C |
| 2 | E | 2 | F |
| 2 | F | 3 | A |
| 2 | F | 3 | D |
| 2 | F | 3 | F |
| 2 | F | 3 | Z |
| 3 | G | 1 | A |
| 3 | G | 1 | B |
| 3 | G | 1 | D |
| 3 | H | 2 | A |
| 3 | H | 2 | B |
| 3 | H | 2 | C |
| 3 | H | 2 | D |

The column entitled Sub_Priority presents medical conditions within each unique combination of class and medical condition (already sorted by priority with a class) in a sorted order that is defined expressly for each combination. That is, sub_priority provides a means by which the conditions in the list can be further sorted to provide additional information related to urgency. For example, problems related to late data transmissions (all within one class and assigned to have one priority) may be displayed in the order of the most overdue first. Subpriorities for each medical condition will be uniquely defined for that condition. In this example, the column labeled sub_priority may be conceived of as representing a "priority score" that can be defined for each condition. Other embodiments may utilize different methods to achieve similar means, and the process of prioritization could also be extended to additional levels as needed (i.e., sub—sub-priorities). Use of a single sub_priority column will support this feature.

Using Table 3, a relationship table may be derived to determine which medical conditions have a higher degree of medical severity than other medical conditions. An exemplary relationship table is illustrated below as Table 4. Conditions may be overridden that are either 1) unrelated but of a lesser priority than those in the first column, or 2) closely related or being of the same "type" and therefore need not be identified and treated since treatment for the most severe form will obviate the need for treatment of less severe conditions of the same type.

TABLE 4

| Medical Condition | Overrides Medical Condition |
|---|---|
| A | D and H |
| B | G |
| D | H |
| E | F and G |

Referring back to FIG. 6, operations for identifying medical conditions (Block 202) based upon Table 3 and Table 4 above are schematically illustrated. Initially a test is performed for medical condition A (Block 204). If transmitted data from a PPM indicates that a patient has medical condition A (Block 206), then tests for medical conditions D and H (Block 208–Block 214) are not performed because medical conditions D and H have lower priority than medical condition A. If transmitted data from a PPM indicates that a patient does not have medical condition A (Block 206), a test for medical condition D is performed (Block 208). If transmitted data from a PPM indicates that a patient has medical condition D (Block 210), then tests for medical condition H (Block 212–Block 214) are not performed because medical condition H has lower priority than medical condition D. If transmitted data from a PPM indicates that a patient does not have medical condition D (Block 210), a test for medical condition H is performed (Block 214).

Whether or not transmitted data from a PPM indicates that a patient has medical condition H (Block 210) or if a patient has medical condition A (Block 206), a test for medical condition B is performed (Block 216). If transmitted data from a PPM indicates that a patient has medical condition B (Block 218), then tests for medical condition H (Block 220–Block 222) are not performed because medical condition H has lower priority than medical condition B. If transmitted data from a PPM indicates that a patient does not have medical condition B (Block 218), a test for medical condition H is performed (Block 220).

Whether or not transmitted data from a PPM indicates that a patient has medical condition H (Block 222) or if a patient has medical condition B (Block 218), a test for medical condition C is performed (Block 224). Whether or not transmitted data from a PPM indicates that a patient has medical condition C (Block 226), a test for medical condition E is performed (Block 228).

If transmitted data from a PPM indicates that a patient has medical condition E (Block 230), then tests for medical conditions F and G (Block 232–Block 238) are not performed because medical conditions F and G have lower priority than medical condition E. If transmitted data from a PPM indicates that a patient does not have medical condition E (Block 230), a test for medical condition F is performed (Block 232). If transmitted data from a PPM indicates that a patient has medical condition F (Block 234), then tests for medical condition G (Block 236–Block 238) are not performed because medical condition G has lower priority than medical condition F. If transmitted data from a PPM indicates that a patient does not have medical condition F (Block 234), a test for medical condition G is performed (Block 238). All medical conditions identified are then stored within a PAC server (Block 240).

It should be further noted that the definition and specification of these medical conditions and their associated priorities, and of the relationship between conditions where the treatment and identification of lower priority condition may be superceded by those of higher priority is configurable. The problem definitions may be configured in part to reflect individual patient differences by adjustment of the default physiologic or behavioral parameters which will trigger the identification of a given problems. Where default values for identification are utilized, patient parameters are inherited from the doctor, and these may in turn be inherited from other, higher levels within the system.

Prioritizing Identified Patient Medical Conditions

According to a preferred embodiment of the present invention, identified patient medical conditions are prioritized based on a hierarchy of medical severity. In general, three classes of medical conditions (Class I, II and III) may be utilized. However, it is to be understood that various numbers and types of classes of medical conditions may be utilized without departing from the spirit and intent of the present invention.

Class I medical conditions are those that require immediate attention based on physiologic or behavioral data collected by a PPM. Although identified by a PAC server, many of these conditions may also be identified by a PPM and may result in prompts to the patient to transmit to a PAC server up-to-date data and to follow this up with a telephone call to the case manager or physician. While late transmissions may not necessarily require immediate action, they may be placed in the Class I category for reasons of health safety.

Class II medical conditions may be significant medical conditions, but may not require immediate medical attention or action on the part of a case manager. Class II medical conditions, if not addressed, may develop into Class I medical conditions that do require immediate attention.

Class III medical conditions are defined as suboptimal conditions in which room for patient improvement may be indicated by physiologic and/or behavioral data collected from a patient's PPM. Many Class III medical conditions may relate to poor or inconsistent compliance with a self-monitoring regimen.

Figure 7:
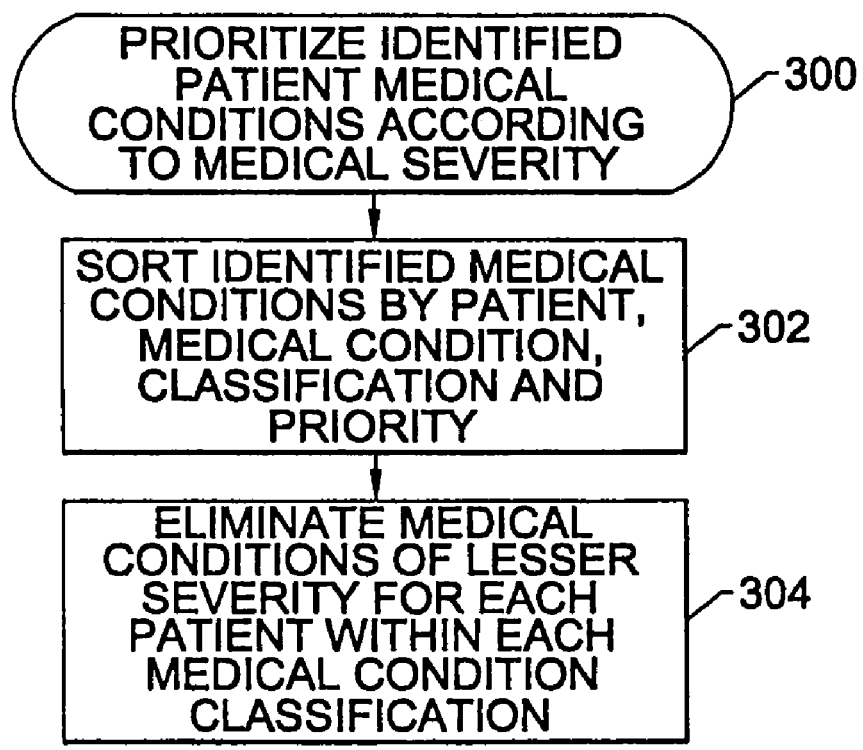
FIG. 7 schematically illustrates operations for prioritizing identified medical conditions according to aspects of the present invention.

Referring now to FIG. 7, operations for prioritizing identified medical conditions according to aspects of the present invention are schematically illustrated. Identified medical conditions are sorted by patient, medical condition, classification, priority and sub-priorities (Block 302). Medical conditions of lesser severity for each patient within each medical condition classification are eliminated (Block 304).

Figure 8:
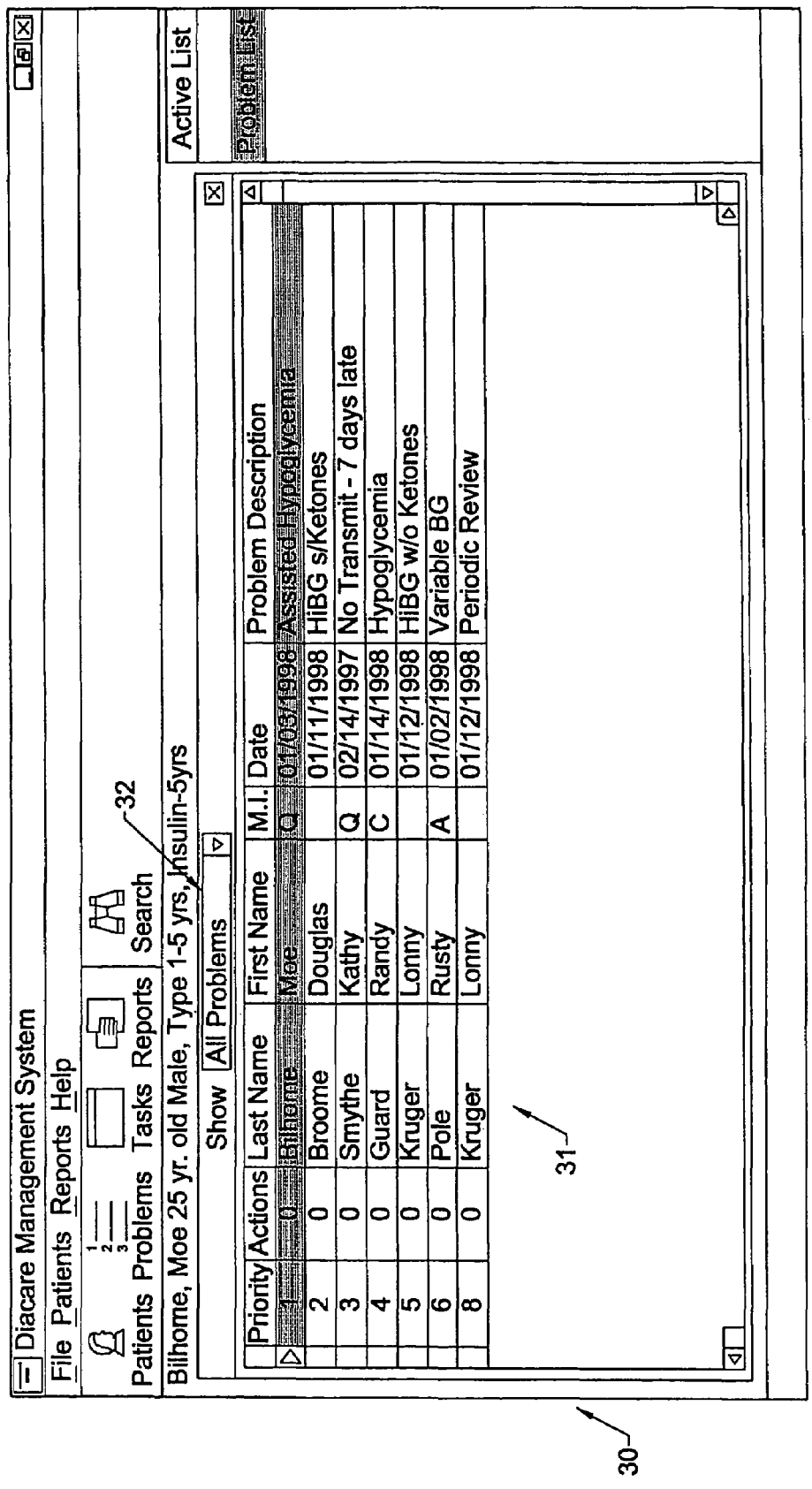
FIG. 8 illustrates an exemplary user interface for displaying medical conditions prioritized according to medical severity.

Displaying Selectable List of Patients with Identified Problems in Priority Order After all medical conditions have been identified, a list of medical conditions for each patient is normalized to eliminate medical conditions of the same type or of lesser severity. Only the remaining medical conditions for a given patient are available for display in a larger list(s) of medical conditions identified for all patients. FIG. 8 illustrates an exemplary user interface 30 wherein a list 31 of medical conditions for a plurality of patients is displayed in priority order. In the illustrated user interface 30, the patient with the highest priority medical condition is listed first. A filter allows a user (case manager) to display various levels of detail of prioritized medical conditions. A box 32 is provided in the illustrated user interface 30 that allows a case manager to select the level of displayed detail. In the illustrated user interface, the filter selection in box 32 allows all identified, prioritized medical conditions of all patients to be displayed.

A list of prioritized medical conditions appears when a case manager first logs into a PAC server via a CMC. The order of presentation is based on medical condition class. Within each class, medical conditions of different types are sorted by an assigned priority. Within each separate medical condition the individual cases are optionally sorted by a severity index. This feature may be defined separately for each type of medical condition, and further may reflect settings that are defined for individual patients as necessary or desirable. For example, late transmissions may be sorted by the number of days overdue, and persistent poor control might be sorted by blood pressure which is chronically elevated.

Figure 9:
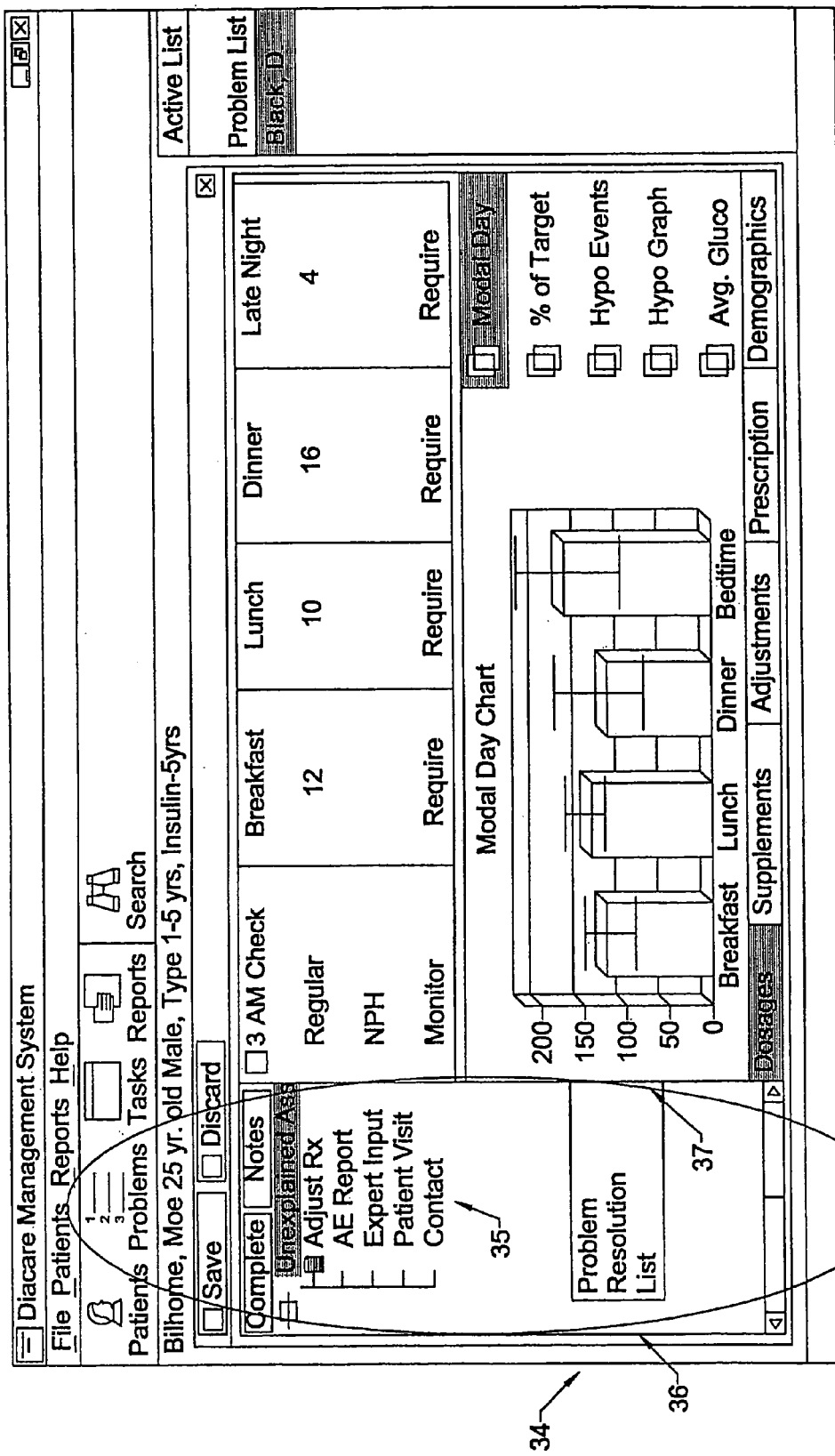
FIG. 9 illustrates an exemplary user interface for displaying patient-specific information.

Preferably, medical conditions having the highest medical severity appear at the top of the list. Selection of a patient medical condition, such as by mouse click, results in a change of the user interface to one focused upon the selected patient, as illustrated in FIG. 9. In the illustrated interface user 34 of FIG. 9, all current medical conditions 35 for the selected patient appear on the left side 36 of the user interface 34 in a list format resembling a directory structure, and the right side 37 of the user interface contains current prescriptive and report data. The listing on the left side resembles a directory structure in form and function, whereby selection of a condition by mouse click will expand the list on the left side to reveal available treatment options for the selected condition. On the right side default screens are available in a tabbed format that can be used to modify medication dosages, parameters related to the adjustment of medication in the PPM, and the fixed and contingent self-monitoring schedule. Changes to these parameters can be directly communicated to the PPM and are summarized in documentary form in a Chart Summary Report. This report and the changed data can also be used, in part, to generate AVM using text to speech technology that verbally summarizes new treatment instruction for the patient. Certain actions or treatment options which may appear below current medical conditions identified for this patient may cause other user windows and dialog boxes to appear, as described below.

Providing Options for Treating Identified Medical Conditions

The selection of a patient medical condition in the user interface of FIG. 9 by mouse click may result in an expanded list of available actions that may be taken for the chosen medical condition. The actions displayed may be only those which have been associated with the specifically-defined (and "expanded") medical condition. Selection of an action for a given medical condition may provide immediate access to user interfaces where dosages or algorithmic alterations can be made (if applicable), or may provide methods for contacting patients.

Communicating Treatment Information to Patient

A variety of specific actions may be undertaken which involve or utilize a patient's PPM. These may include the adjustment of medication dosage level or the timing for administration; adjustment of the rules or algorithmic parameters which a PPM or PAC server uses to independently adjust and alter medication dosage (e.g., alteration of the target range for the physiologic function being monitoring); alteration of the patient's self-monitoring schedule; or alteration of the parameters that trigger additional or contingent self-monitoring suggestions in the PPM. In addition to these parameters, a case manager may also select and/or compose messages to be downloaded to a patient's PPM, or transmitted via telephone, AVM, e-mail and facsimile transmission, which are designed to reinforce correct behaviors or alter maladaptive behaviors. A case manager may also compose a message asking a patient to schedule an office visit with a physician, and may also alter a PPM's transmission schedule (which may take affect following the next transmission). Special messages related to scheduling office appointments ask the patient to make an appointment with a named professional and provide his or her phone number. The PPM may query the patient on a daily basis concerning whether the appointment has been made, and then solicit the appointment date for uploading to the PAC. After the appointment date has passed, the PPM can query the patient to ascertain if the appointment was actually kept.

Preferably, screening mechanisms are provided for ensuring that treatment or information provided by a case manager is medically qualified for a particular patient before the treatment or information is communicated to a patient or to a patient's PPM.

Figure 10A:
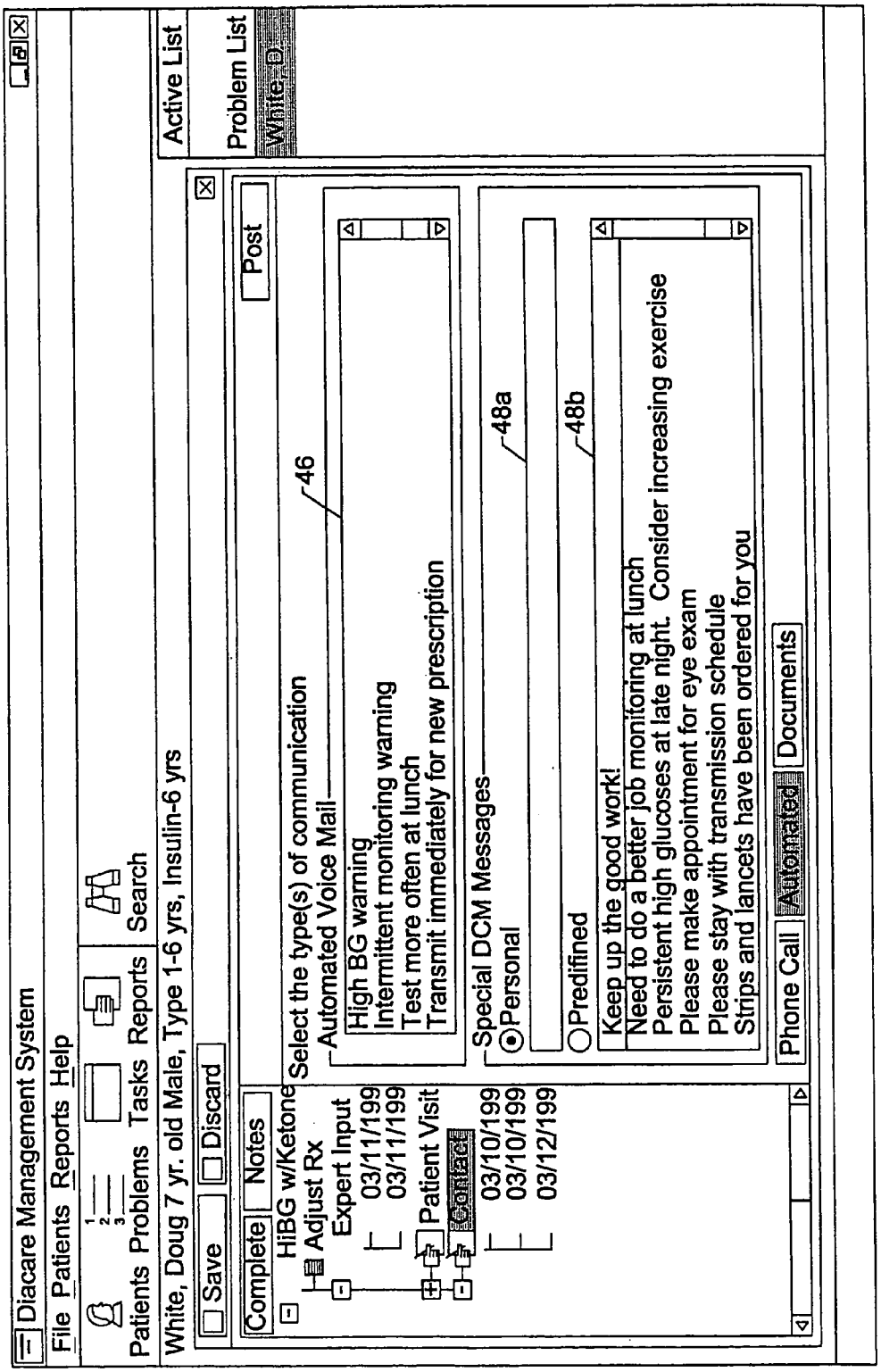
Figure 10B:
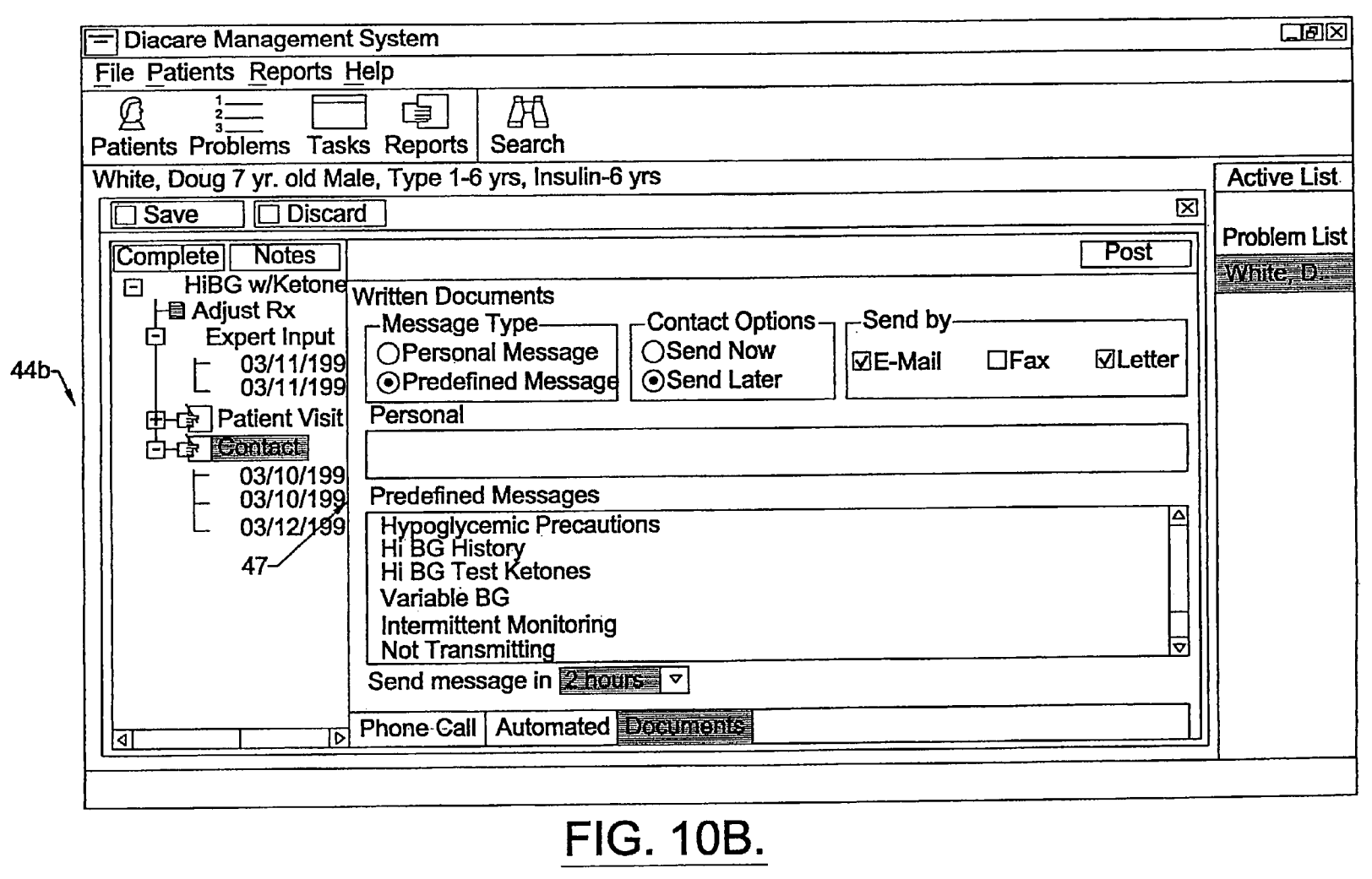
Figure 10C:
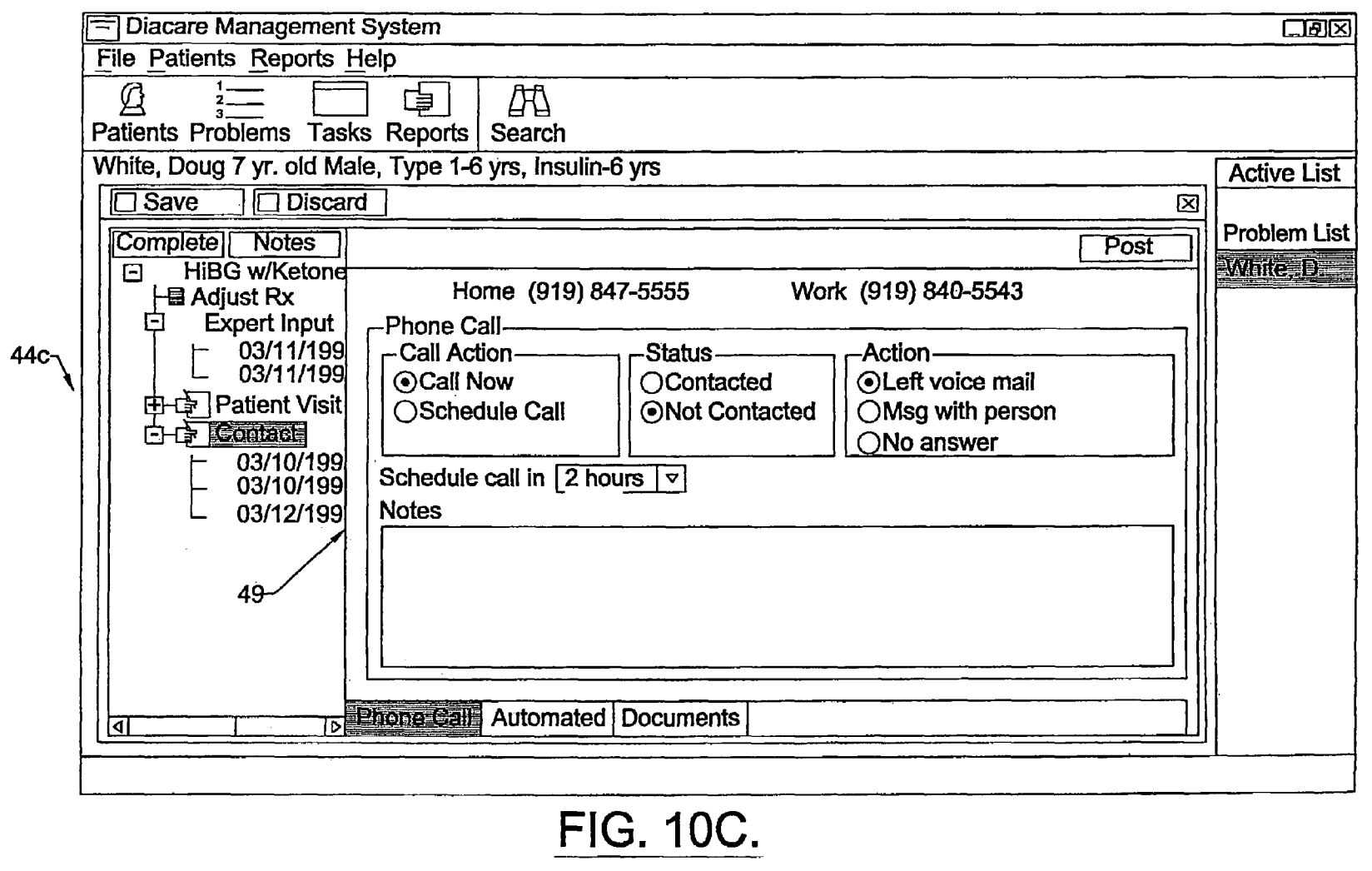

Exemplary user interfaces 44a, 44b, 44c for communicating with a patient, are illustrated in FIGS. 10A–10C, respectively. In FIG. 10A, automated voice mail (AVM) messages can be selected and sent to a patient via the box 46. In addition, personal and predefined messages can be created and/or selected via boxes 48a and 48b, respectively, and transmitted directly to a patient's PPM. In FIG. 10B, various written documents can be selected and sent to a patient via the box 47. These notices can be sent via letter, fax, or e-mail, and can be personal or predefined. In FIG. 10C, status of communications with a patient can be monitored using various features illustrated in box 49.

Once a change has been made in any of the above areas which utilize a patient's PPM, a case manager may optionally elevate the new dosage prescription to a high priority. In the present invention this may cause delivery of a voice message to the patient that he or she should immediately initiate communications between the patient's PPM and a PAC server in order to receive a revised treatment regimen, including, but not limited to, modified medication doses, modified dosage algorithm(s), and modified fixed and contingent self-monitoring schedules and parameters. If a case manager elects not to elevate the revised monitoring parameters to a high priority level, the altered parameters may be loaded automatically during the next routine data transmission which is prompted by the patient's PPM according to the last transmission.

To make a newly saved prescription (e.g., modified medication doses, modified dosage algorithm(s), and modified fixed and contingent self-monitoring schedules and parameters) available to a patient, a case manager "publishes" the prescription. Publishing a prescription means that an altered prescription, which may be conveyed to a patient via a PPM, is finalized to a point where it is officially ready to be given to the patient. An exemplary user interface 54 for adjusting a patient's physician-prescribed medicine dosage (one of several options) via a patient's PPM is illustrated in FIG. 11. A case manager may see up to four columns of information representing four daily quadrants in which adjustments may be enabled for drugs like insulin that have a short half-life. In the case of anticoagulation therapy with warfarin, adjustments in medication are likely to be enabled once or twice per week. The adjustment parameters may appear in a quadrant in which the medication dosage being adjusted is assessed.

Figure 12:
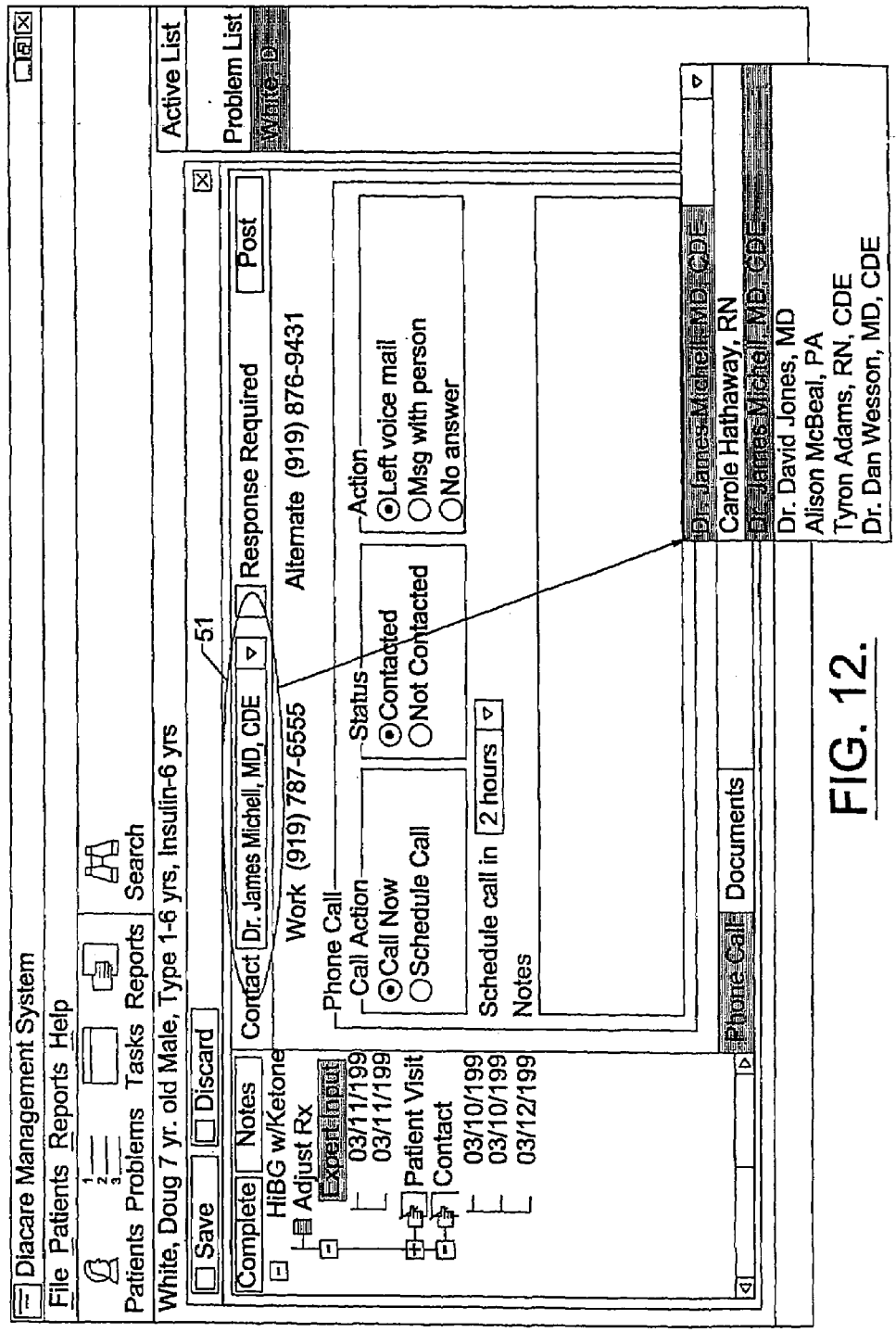
FIG. 12 illustrates an exemplary user interface for seeking input from other medical experts.

In cases where case managers have questions concerning a patient's medical condition or prescription, case managers may seek input from medical experts using a user interface such as that illustrated in FIG. 12. Expert input may be obtained at any step in the review and alteration process, and may involve referencing current patient data and unresolved medical conditions (if any) with a request for help. Expert input may be directed to a superior (e.g., a supervising case manager or the primary care physician), a specialist or to a collateral person involved in the patient's care (e.g., a dietitian, optician, neurologist, hematologist, cardiologist or podiatrist).

In the illustrated user interface 50 (FIG. 12), expert input may be obtained by selecting a health care giver from the box 51. Preferably, various methods of contacting a selected health care giver are available (e.g., telephone, fax, e-mail, office visit, and the like). Contacts with experts may or may not be accompanied by referenced or attached patient data available from the PAC server. Expert input can be directed to people who may not have direct access to the PAC server and be able to directly review patient data (e.g., a podiatrist), but are more typically directed to others with access to the system and are focused on the patients current medical conditions and overall treatment regimen (neurologist, hematologist, endocrinologist or primary care physician). These latter personnel may be expected to provide either advise in written or other form, or may act directly upon (and publish) the overall treatment regimen (medication dosages, dosage adjustment algorithm, or the fixed or contingent self-monitoring schedule) which may be conveyed to the Patient's PPM.

In addition to communicating with patients via a PPM, a case manager may communicate with patients in various ways, such as via telephone, e-mail, AVM and facsimile transmission. Preferably, the present invention provides pre-composed text for inclusion in text-based communications such as letters, faxes and e-mail directed to a patient. Multiple selections can be added to a letter and then edited, or the entire communication can be created manually, and delivery of the text may be done redundantly. Telephone communications may also be managed from a content screen where topic issues can be displayed and optionally highlighted for documentary reasons, and a case manager may elect to immediately make or schedule a patient call, or to schedule voice message delivery of pre-composed or personalized text. Prompting patients to make an overdue transmission of data from his/her PPM to a PAC server may be accomplished using voice message delivery of a pre-composed message. Patient contact options may also be tied to a tickler system to facilitate timely follow-up.

Figure 13:
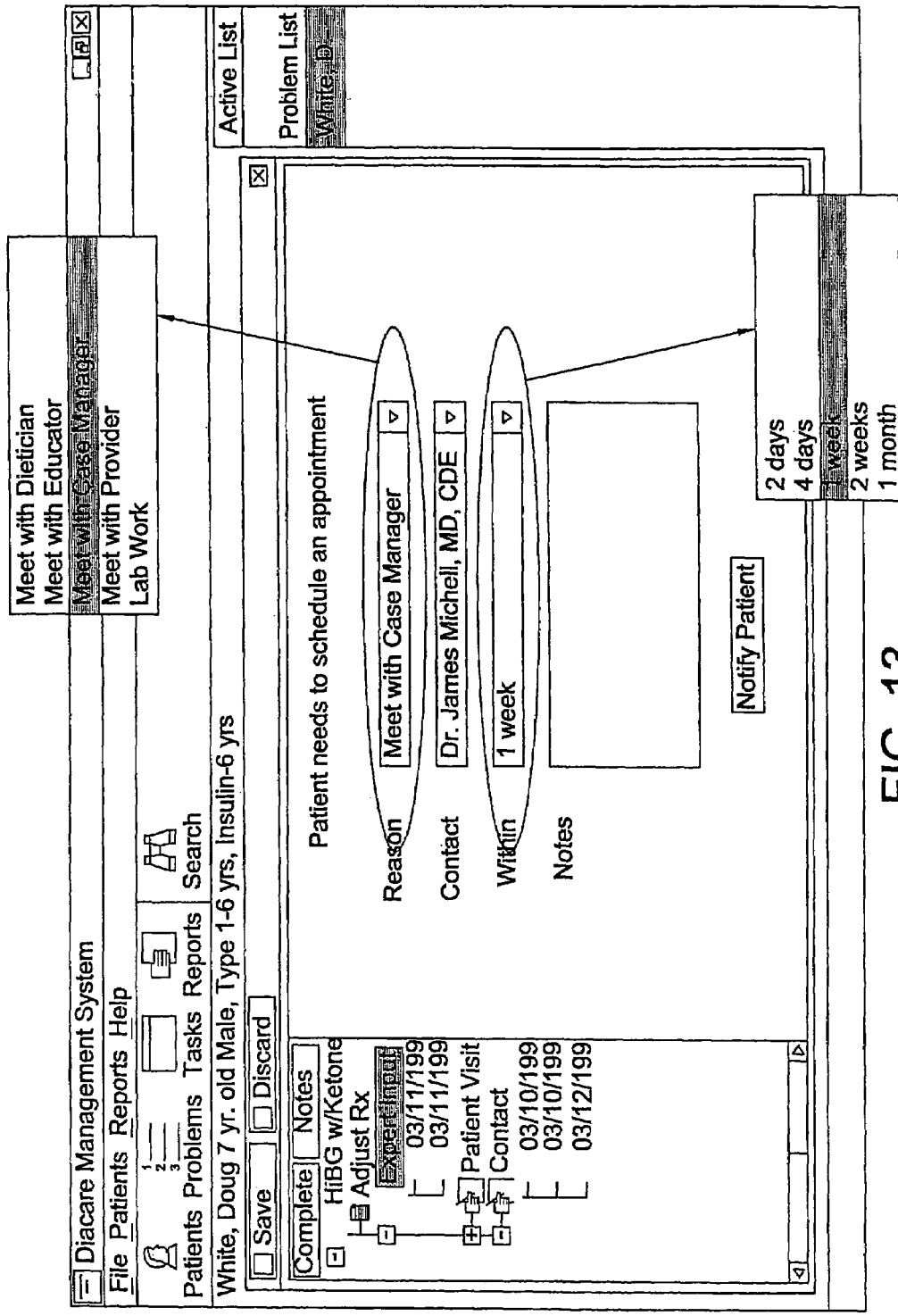
FIG. 13 illustrates an exemplary user interface for facilitating and tracking patient appointments with clinic personnel or other health care providers.

In addition, case managers may utilize the present invention to facilitate and track patient appointments with clinic personnel or other providers involved in health care. An exemplary user interface 56 for this purpose is illustrated in FIG. 13. Once a decision is made to schedule a patient appointment, a system task reminder may be generated that requires periodic follow-up until a record of a scheduled appointment time is input into a PAC server. A case manager may employ a patient's PPM to prompt the patient to make an appointment, and subsequently query the patient for the appointment date once it has been made. Other contact methods may also be employed to prompt a patient to make an appointment and subsequently to inform the case manager concerning the date (e.g., via e-mail, AVM, telephone, and facsimile transmission). A PPM may also be used to verify appointment compliance.

Preferably, the present invention also tracks appointment compliance (e.g., whether a patient kept his/her appointments). Healthcare providers can be sent communications to confirm whenever an appointment has been kept by a patient and to supply associated lab or examination data to a PAC server. To track appointment compliance with providers who cannot directly access a PAC server, a case manager may generate correspondence and associated follow-up reminders in order to obtain confirmation and associated clinical data if desired.

According to another aspect of the present invention, a blind actuarial review of changes made to the medication dosages and/or the rules utilized by a PPM to independently adjust these doses may be utilized. Statistical analysis may optionally be performed on published prescriptions that utilizes pattern analysis, multiple regression, time series and other types of analyses that compare current patient data sets to earlier data and to data of other appropriate patients. This assessment procedure is designed to screen for potential medical conditions whose probability has markedly increased as a result of the most recent prescriptive changes made to a patient's PPM-supported treatment regimen. A secondary purpose involves alerting a case manager in situations where changes made to a prescription are unlikely to result in any significant improvement in a patient's current physiologic condition. In addition, the present invention is also designed to focus a case manager's attention on the areas of a prescription where intervention is likely to result in the greatest improvement in a patient's medical condition.

Figure 14:
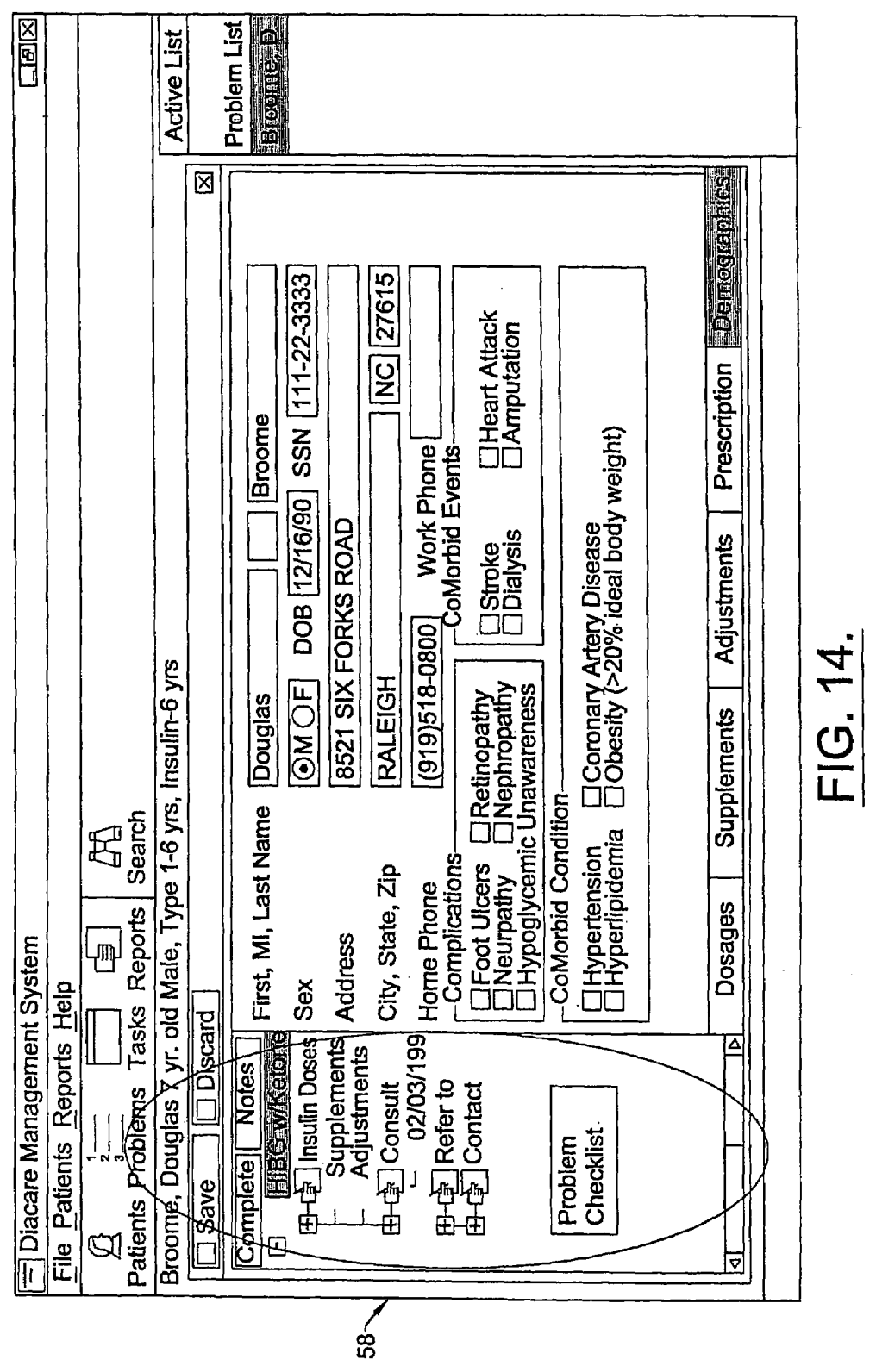

When a medical condition has been corrected, it is effectively removed from a patient's active list by use of a "Complete" button. The user interface 58 of FIG. 14 illustrates a patient's medical condition being removed from the active list. This is graphically illustrated by the addition a check mark in front of the medical condition.

Anticoagulation Therapy

According to another embodiment of the present invention, a portable patient monitor (PPM) as described above may serve as a standalone device for monitoring and adjusting patient-administered medication and testing regimens used in therapy for various diseases. The following describes methods and apparatus for monitoring anticoagulation therapy according to various embodiments of the present invention wherein a warfarin treatment regimen and a prothrombin time (PT) test regimen are utilized. However, it is understood that therapy for other diseases may be monitored in accordance with the present invention including, but not limited to cancer, seizure disorders, depression, asthma and high blood pressure.

Anticoagulation therapy typically includes a medication (e.g., warfarin) regimen and a coagulation test regimen, such as a prothrombin time (PT) test (see, TABLE 1 above for other tests), for a patient. Hereinafter, any reference to "PT test" shall mean "coagulation test" and shall include all coagulation tests utilized in anticoagulation therapy.

A PPM, such as the PPM 20 illustrated in FIG. 2, and described in copending U.S. patent application Ser. No. 09/042,048, filed on Mar. 13, 1998, which is incorporated herein by reference in its entirety, when utilized to monitor disease therapy in accordance with this embodiment of the present invention is referred to as a COAGCARE™ Patient Monitor (CPM). A CPM may include all the features of a PPM described above and also includes computer code that receives and stores patient data provided by a patient. A Palm Pilot, available from 3Com Corporation, Santa Clara, Calif., may be provided with various program code to implement aspects of the present invention.

The term "receives" is intended to include any method of receiving data including, but not limited to, input provided via keyboard or keypad, input provided via cable connection, input provided via infrared, RF, or other wireless connection, and the like.

Exemplary patient information (data) may include physiological data, pathophysiological data, biological data, psychological, neuoropsychological and behavioral data. For example, a CPM may be configured to prompt for and receive data pertaining to hemorrhagic and non-hemorrhagic conditions, signs or symptoms that a patient assesses, has experienced or is experiencing currently. A CPM also may include a medication algorithm that utilizes various patient data to modify warfarin and PT time test regimens in real time. In addition, a CPM may include computer code that communicates modified medication and PT test regimens to a patient. A CPM may also includes computer code that can communicate with a remotely located data processing system, such as a PAC server described above, and that can transmit stored patient data thereto.

A CPM may also include computer code that can prompt a patient to provide information about the patient's compliance with a warfarin regimen and with a PT test regimen during a preceding time period. A CPM also may include computer code that communicates information regarding warfarin dosage to a patient in response to determining that the patient did not comply with a warfarin regimen in a preceding time period.

Typically, a patient will interact with a CPM, such as that illustrated in FIG. 2, on a daily basis to assess data, signs, conditions, symptoms, behaviors and compliance with one or more prescribed medication regimens. With respect to anticoagulation therapy, a CPM contains a PT testing schedule that can be individually prescribed via the CPM. The CPM will prompt a patient to perform and store PT test results according to an individualized schedule, and to test in response to certain signs, conditions, symptoms (data as defined previously) that are evaluated by the CPM. A CPM may be configured to prompt a patient for testing which is contingent upon self-reports of alarming conditions, signs or symptoms (data) of either a supra-therapeutic and/or sub-therapeutic nature).

A CPM also may include computer code that assesses changes in patient behavior that may affect warfarin therapy on a daily (or other time period) basis. Changes in a patient's diet, medication, illness, or vitamins are flagged for potential telephone follow-up by a healthcare provider following the patient's next data transmission from the CPM to a remotely located data processing system, such as a PAC server, which was described in detail above. Patients are prompted by the CPM to indicate any warfarin or other medication dosage additions, changes, discontinuations, or omissions. Vitamin intake by a patient also can be assessed for impact to PT testing. Patients are also prompted by the CPM to identify any significant dietary changes such as eating more or less than usual, or major changes in dietary composition. Conditions that can affect warfarin therapy, such as illness, vomiting, and diarrhea, can also be assessed by the CPM.

Referring now to FIGS. 15–19, operations for monitoring anticoagulation therapy via a remote and preferably portable patient apparatus (CPM) according to the present invention are illustrated. It is understood that the present invention may be used for monitoring therapies for other diseases and conditions including, but not limited to, high blood pressure, depression, seizure disorders, cancer, and asthma. In the illustrated embodiment of FIGS. 15–19, the described anticoagulation therapy includes a warfarin medication regimen and a PT test regimen. Wherever the term "warfarin" is used, it is understood that the term "medication" may be substituted therefor.

Figure 15:
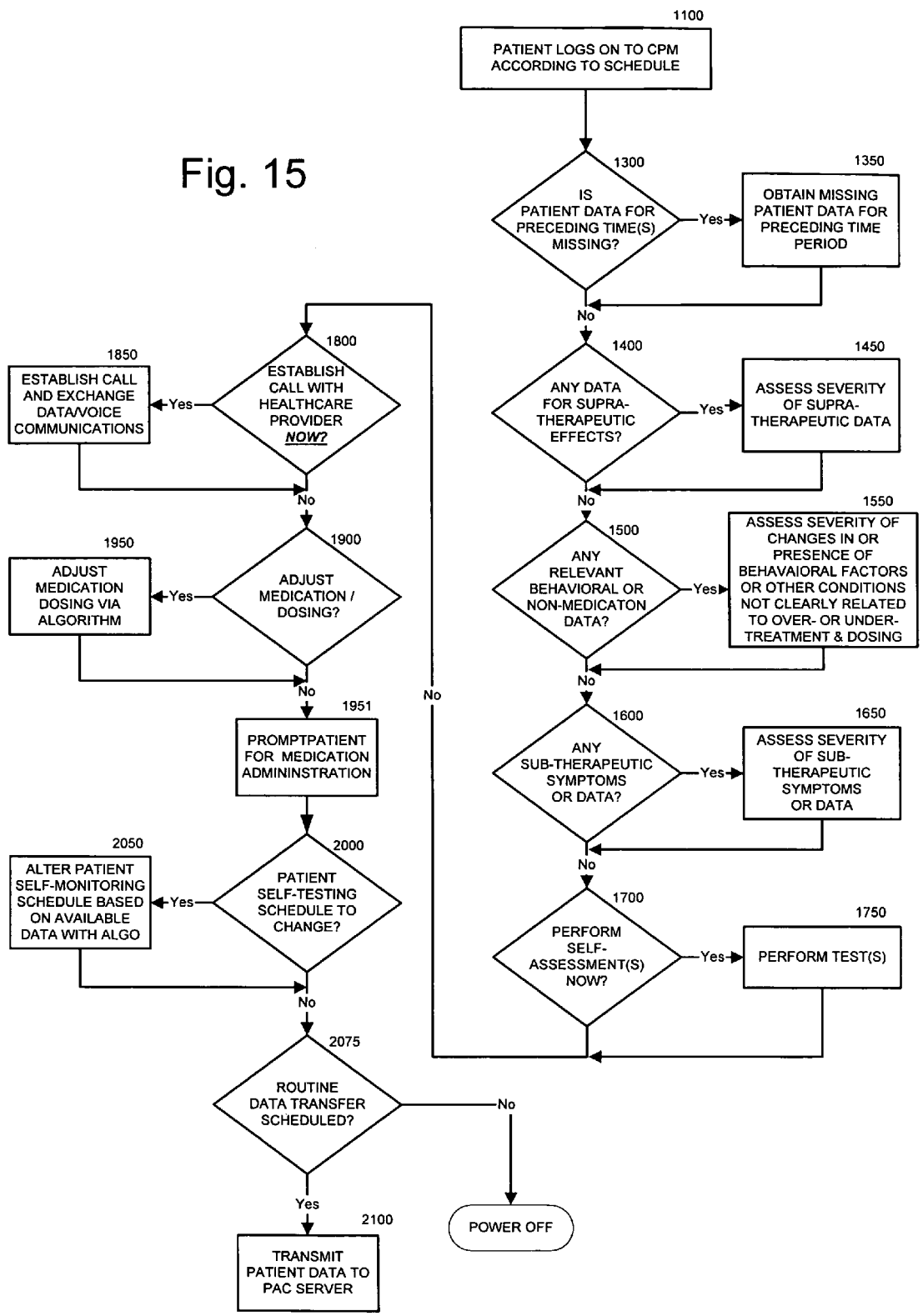
FIGS. 15–19 schematically illustrate operations for monitoring anticoagulation therapy via a patient apparatus according to one embodiment of the present invention.

Referring initially to FIG. 15, a patient undergoing anticoagulation therapy logs onto his/her personal CPM (Block 1100) according to a predefined schedule (for example, a daily schedule). If the CPM determines that information (or data) regarding the patient's warfarin and PT test regimens (or other aspects of the anticoagulation therapy) is missing or insufficient (i.e., that the patient has not entered this information into the CPM during a preceding time period, or has not complied with an established warfarin regimen and/or PT test regimen) (Block 1300), the CPM initiates a procedure for obtaining the missing patient data (Block 1350).

Figure 16:
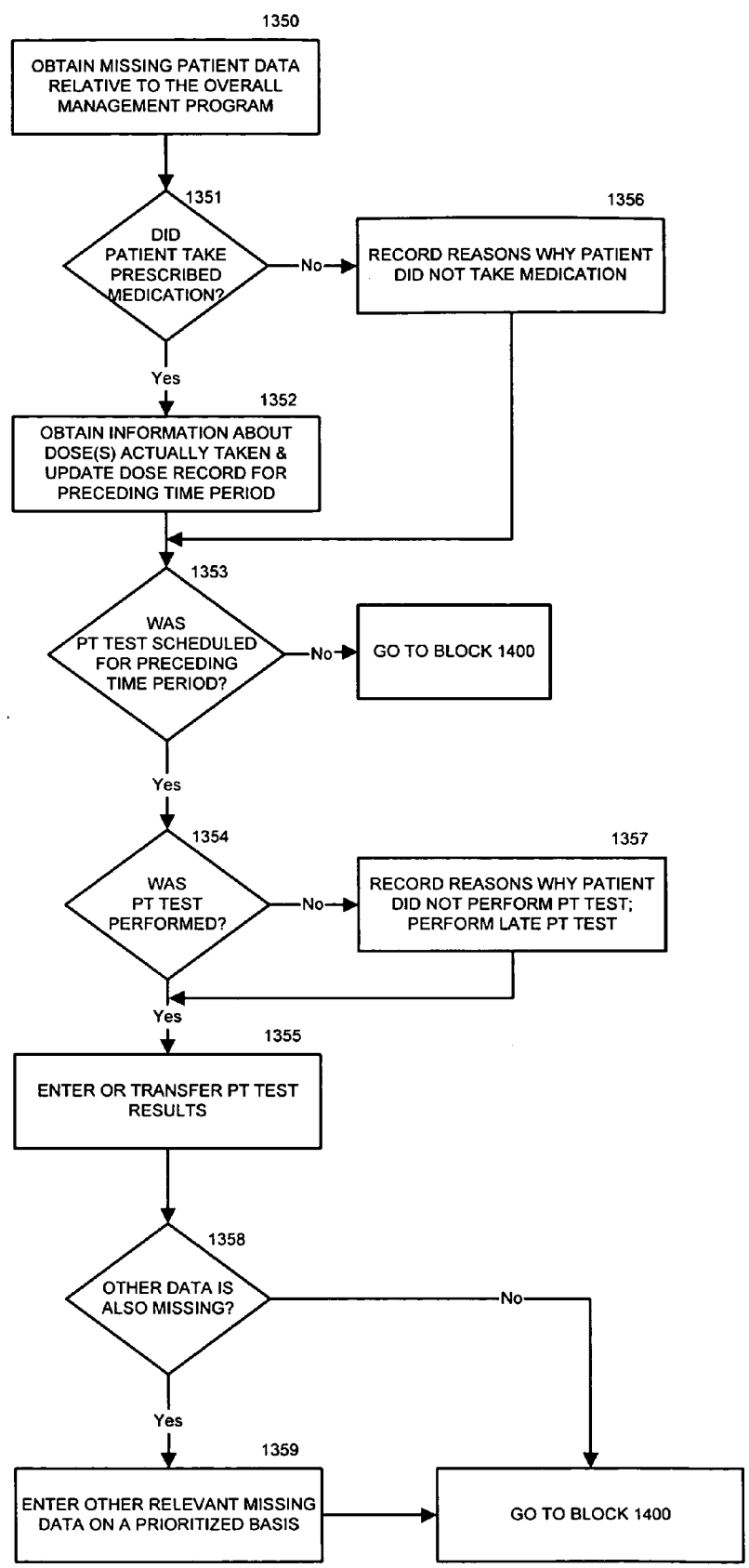

It is understood that missing patient data as described herein with respect to Block 1350 and FIG. 16 is not limited to medication and test results. Missing patient data may also include signs, conditions, symptoms, compliance with exercise regimens, confirmation of injection sites that could affect drug absorption (heparin agents), prompts to calibrate or test calibration of biological or physiological testing equipment, patient apparatus maintenance, and the like.

Referring to FIG. 16, a procedure for obtaining the missing patient data (Block 1350) regarding the warfarin and PT test regimens (or other aspects of the anticoagulation therapy) is illustrated. The CPM prompts the patient to indicate whether the patient took his/her prescribed dosage of warfarin in the preceding time period of interest (Block 1351). If the patient responds "No", the CPM prompts the patient for reasons why the patient did not take the warfarin according to the prescribed regimen and records these reasons (Block 1356). Operations then return to Block 1353.

With respect to Block 1356, a check list is preferably provided via a user interface that allows a patient to indicate reasons (e.g., forgot to take medication, ran out of medication, and the like). If the patient responds "Yes" (Block 1351), the CPM obtains information from the patient about a dose(s) actually taken and updates a dose record(s) for the preceding time period of interest (Block 1352).

The CPM then makes a determination whether a PT test was scheduled for the preceding time period of interest (Block 1353). If the answer is "No", operations return to Block 1400 (FIG. 15). If the answer is "Yes", the CPM prompts the patient whether the PT test was performed (Block 1354). If the CPM determines that the PT test was not performed the CPM prompts the patient for reasons why the PT test was not performed and records these reasons (Block 1357). The patient may also be prompted to perform the PT test at this time (Block 1357) and to enter the PT test results (Block 1355). If the CPM determines that the patient did perform the PT test (Block 1354), the CPM prompts the patient to enter the test results (Block 1355).

A determination is then made whether other data is missing (Block 1358). If the answer is "Yes", the missing data is entered, preferably on a prioritized basis (Block 1359). If the answer is "No", operations then return to Block 1400 (FIG. 15).

Referring back to FIG. 15, the CPM prompts the patient as to whether the patient has experienced (or is experiencing) any supra-therapeutic signs, conditions or symptoms (collectively referred to as "data") (Block 1400). As is well known to those of skill in the art, a supra-therapeutic sign or condition is data which indicates a patient has taken too much of a medication (over-dose). With respect to anticoagulation therapy, hemorrhagic "signs", such as bleeding, bruising, thinning blood, blood in urine or stool, severe headache, other bleeding, swollen joints, and cuts that will not stop bleeding are exemplary supra-therapeutic data. If the answer at Block 1400 is "Yes", the CPM initiates a procedure for assessing the severity of the supra-therapeutic signs and conditions (Block 1450).

Figure 17:
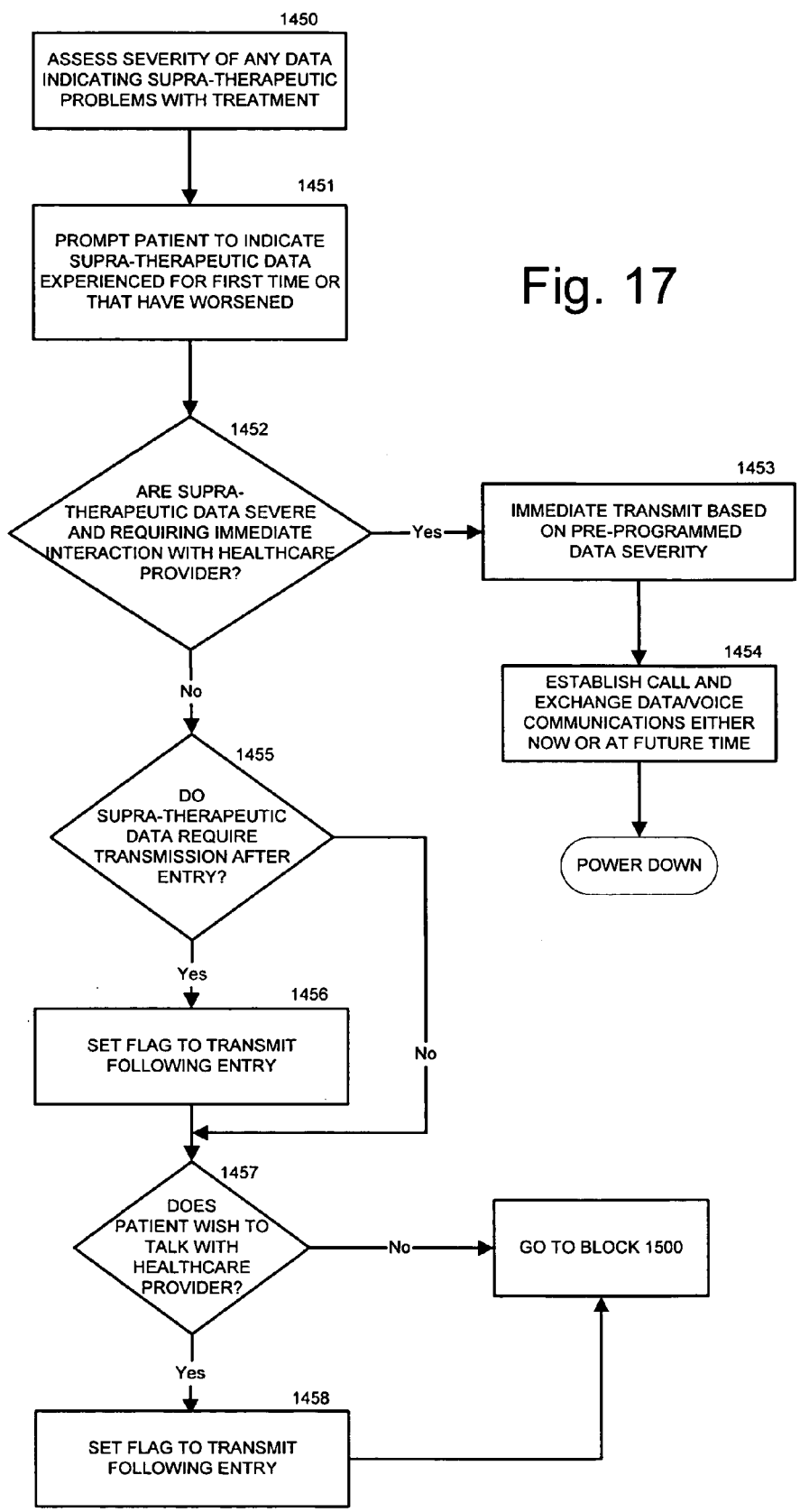

Referring to FIG. 17, a procedure for assessing the severity of supra-therapeutic conditions experienced by a patient (Block 1450) is illustrated. The CPM prompts the patient to indicate supra-therapeutic conditions that the patient is either experiencing for the first time, or that have worsened (Block 1451). A check list is preferably provided via a user interface that allows a patient to indicate the supra-therapeutic symptoms. The CPM makes a determination at Block 1452 whether the supra-therapeutic conditions indicated by the patient are severe and require immediate communication to a healthcare provider. If the answer is "Yes", information about the supra-therapeutic symptoms is communicated immediately to a healthcare provider (Block 1453) via a communications network. The CPM may also instruct the patient to call his/her healthcare provider immediately, or to call for emergency medical attention (Block 1454). The CPM may be configured to automatically establish voice communications with a healthcare provider or emergency medical service for the patient.

If the answer at Block 1452 is "No", the CPM determines whether information about the supra-therapeutic signs or conditions are serious enough to require communication to a healthcare provider after completing the entry or interaction with the CPM; i.e., transmissions will occur as part of this interactive session, as opposed to the preset schedule (Block 1455). If the answer at Block 1455 is "Yes", the CPM sets a flag to transmit the supra-therapeutic data to a healthcare provider's PAC system immediately following or at the conclusion of this entry or interaction with the CPM (Block 156). If the answer at Block 1455 is "No", the CPM then prompts the patient to determine whether the patient wishes to talk with a healthcare provider about the signs, conditions or symptoms ("data" or anything else that is of concern) (Block 1457). If the answer at Block 1457 is "No", operations are returned to Block 1500 (FIG. 15). If the answer at Block 1457 is "Yes", the CPM sets a flag to transmit supra-therapeutic symptom information to a healthcare provider following entry. (Block 1458). Operations are then returned to Block 1500 (FIG. 15).

Referring back to FIG. 15, the CPM prompts the patient as to whether the patient has undergone any behavioral or non-medication related changes (Block 1500). For example, has the patient changed his/her diet and/or intake of vitamins and/or other medications. Behavioral and non-medication related changes include all signs, symptoms, conditions and behavior (changed or otherwise of concern) that could affect a patient's disease state, and which are not directly attributable to too much medication (supra-therapeutic) or too little medication (sub-therapeutic). According to the present invention, behavioral and non-medication related changes may be divided into those that are serious (thus requiring a call to a healthcare provider immediately) and those that bear watching. Behavioral and non-medication related changes that only bear watching may become significant if they are deemed to alter the patient's medication schedule or schedule for transmitting data to a healthcare provider.

If the answer at Block 1500 is "Yes", the CPM initiates a procedure for assessing the severity of changes in or presence of behavioral factors or other conditions that are not clearly related to supra-therapeutic or sub-therapeutic conditions (Block 1550).

Figure 18:
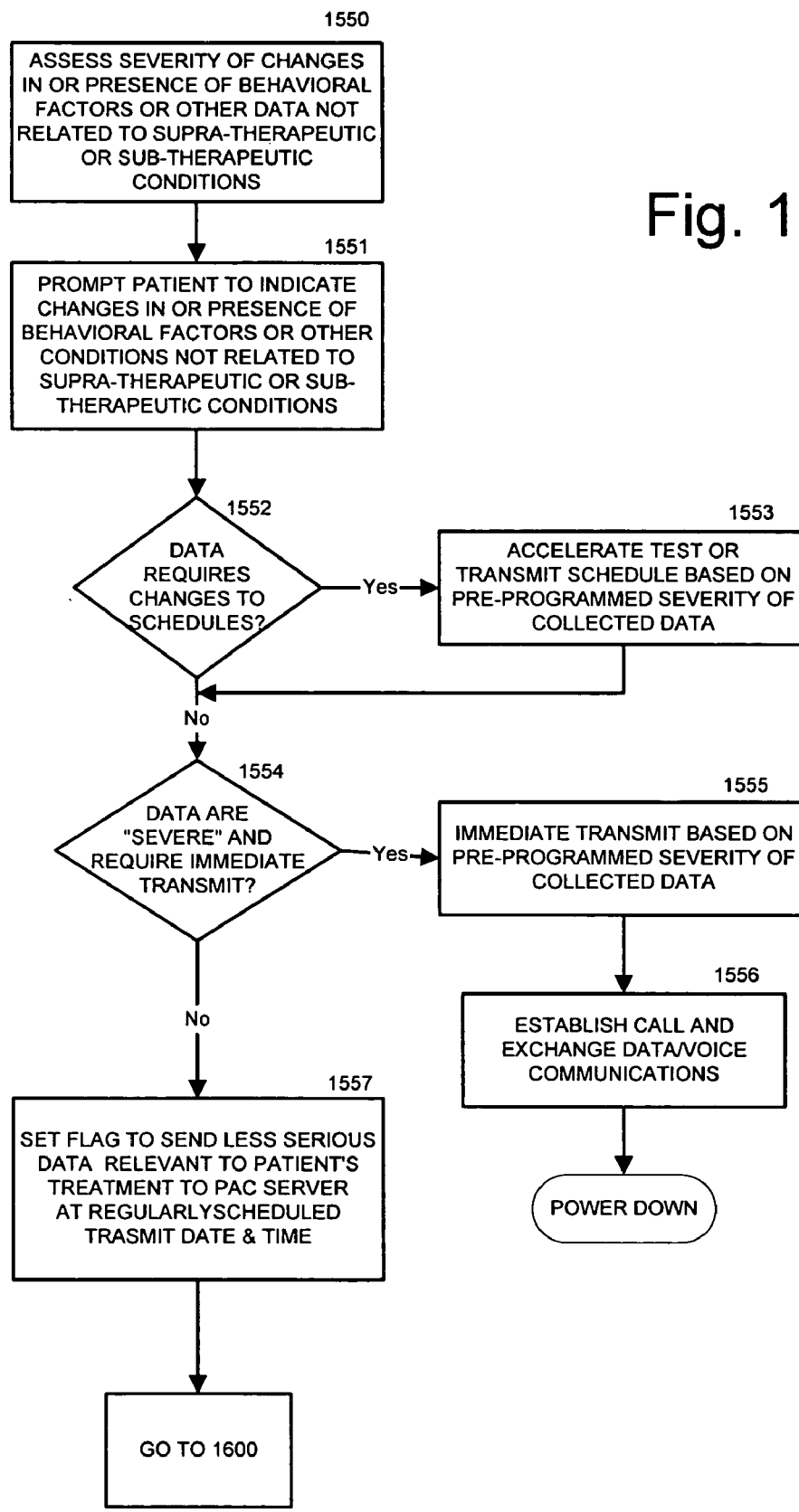

Referring to FIG. 18, a procedure for assessing the severity of changes in or presence of behavioral factors or other conditions that are not clearly related to supra-therapeutic or sub-therapeutic conditions (Block 1550) is illustrated. The CPM prompts the patient to indicate changes in or presence of behavioral factors or other conditions that are not clearly related to supra-therapeutic or sub-therapeutic conditions (Block 1551). A check list is preferably provided via a user interface. Exemplary check list items may include whether a patient has changed vitamins/medications, whether a patient has changed dosages of vitamins/medications, whether a patient has stopped taking vitamins/medications, whether the patient is eating more or less, and whether the patient is eating different foods.

The CPM then determines whether the information provided by the patient regarding changes in or presence of behavioral factors or other conditions that are not clearly related to supra-therapeutic or sub-therapeutic conditions requires changing (e.g., accelerating) a testing regimen or an established data transmission schedule (Block 1552). If the answer is "Yes" the patient's testing and/or data transmission schedules are modified (Block 1553) by the CPM. Operations return to Block 1554.

If the answer at Block 1552 is "No", the CPM determines whether the information provided by the patient regarding changes in or presence of behavioral factors or other conditions that are not clearly related to supra-therapeutic or sub-therapeutic conditions are severe enough to warrant immediate transmission to a healthcare provider (Block 1554). If the answer is "Yes", the information provided by the patient regarding changes in or presence of behavioral factors or other conditions that are not clearly related to supra-therapeutic or sub-therapeutic conditions is immediately transmitted to a healthcare provider (Block 1555). The CPM may then establish a call with a healthcare provider for the patient (Block 1556).

If the answer at Block 1554 is "No", the CPM sets a flag (i.e., a reminder) to send the information provided by the patient regarding changes in or presence of behavioral factors or other conditions that are not clearly related to supra-therapeutic or sub-therapeutic conditions to a healthcare provider according to a regular data transmission schedule (Block 1557). Operations are then returned to Block 1600 (FIG. 15).

Referring back to FIG. 15, the CPM prompts the patient as to whether the patient is experiencing any sub-therapeutic symptoms, signs or conditions (Block 1600). If the answer is "Yes", the CPM initiates a procedure for assessing the severity of sub-therapeutic conditions (Block 1650).

Figure 19:
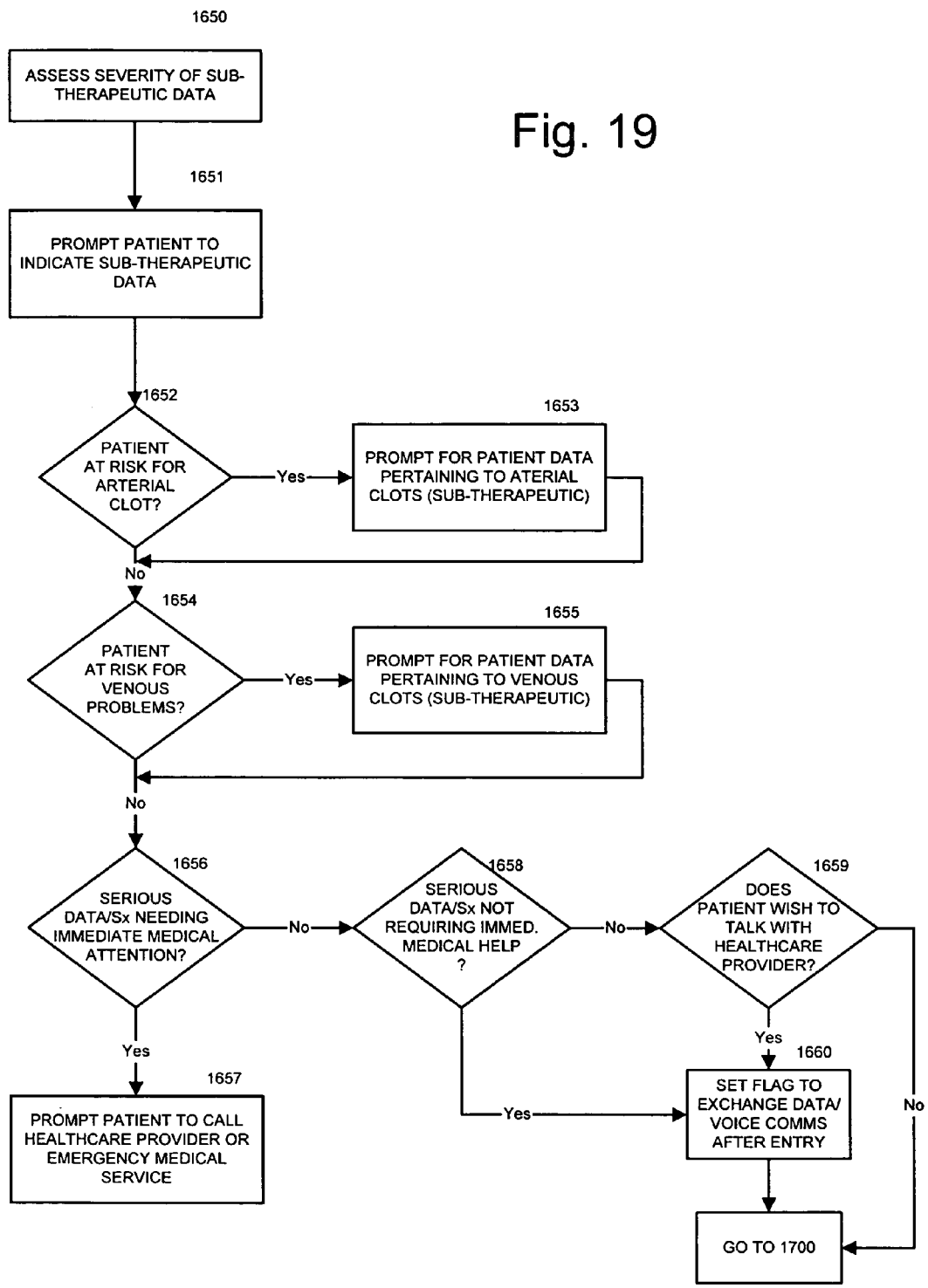

Referring to FIG. 19, a procedure for assessing the severity of sub-therapeutic conditions experienced by a patient (Block 1650) is illustrated. The CPM prompts the patient to indicate supra-therapeutic signs, conditions or symptoms that the patient is either experiencing for the first time, or that have worsened (Block 1651). As is known to those of skill in the art, sub-therapeutic conditions related to anticoagulation therapy include non-hemorrhagic signs, symptoms or conditions ("data"), such as fever, vomiting, diarrhea, and the like. A check list is preferably provided via a user interface that allows a patient to indicate sub-therapeutic data.

The CPM then determines, based on the provided sub-therapeutic symptom information, whether the patient is at arterial risk (i.e., at risk of arterial clot) (Block 1652). If the answer is "Yes", the CPM prompts the patient to indicate whether he/she is experiencing new signs, symptoms or conditions, such as muscle weakness, slurred speech, chest pains, and blindness or other vision problems (Block 1653). The CPM then determines, based on the provided information about new signs, symptoms or conditions (data), whether the patient is also at risk for venous conditions (Block 1654). That is, the CPM determines whether the patient's symptoms or signs may be indicative of a heart attack or stroke. If the answer is "Yes", the CPM prompts the patient to indicate whether he/she is experiencing new venous signs or symptoms such as swollen or hot arms and/or legs, chest pain, and shortness of breath (Block 1655).

The CPM then determines whether the patient's health data (venous and/or arterial) require immediate medical attention (Block 1656). If the answer is "Yes", the CPM prompts the patient to call a healthcare provider or to call for other emergency medical attention (Block 1657). A CPM may be configured to automatically establish voice communications with a healthcare provider or emergency medical service for the patient. The existence of serious arterial signs, symptoms or conditions may cause the CPM to inhibit warfarin (and other medication) dosage recommendations until the data have been reviewed by a healthcare provider.

If at Block 1656 the CPM determines that the patient's data are such that they do not require immediate medical attention, the CPM then determines whether the data should be reviewed as soon as the CPM entry session is complete (CPM has acquired all data) but before medication is actually recommended, or whether the entry can be completed with medication recommended—but with the contents of the entry to be logged and screened immediately following the interactive CPM session (Block 1658).

If at Block 1658 the answer is "No", the CPM prompts the patient to determine whether the patient wishes to talk with a healthcare provider about any identified or questionable signs, symptoms or conditions (Block 1659). If the answer is "No", operations are returned to Block 1700 (FIG. 15). If the answer at Block 1659 is "Yes", the CPM sets a flag to transmit the symptom information to a healthcare provider, either now or at a future time (Block 1660). Operations are then returned to Block 1700 (FIG. 15).

Similarly, if the CPM determines at Block 1658 that the patient's conditions is not serious enough to require immediate medical attention (i.e., the answer is "Yes"), the CPM sets a flag to transmit the symptom information to a healthcare provider, either now or at a future time (Block 1660). Operations are then returned to Block 1700 (FIG. 15).

Referring back to FIG. 15, the CPM assesses the need for the patient to self-perform PT testing at the present time (Block 1700). With respect to anticoagulation therapy, a CPM typically will conclude that testing should be performed if a patient has signs or symptoms of bleeding or clotting, or changes in diet or other medications, illness, vomiting, diarrhea, or if the minimum interval between tests has been exceeded. If the CPM determines that testing should be performed, the CPM prompts the patient to perform the PT test and enter the results in the CPM (Block 1750).

If the CPM determines that testing need not be performed, the CPM assesses the need to establish a call with a healthcare provider at the present time (Block 1800). With respect to anticoagulation therapy, a CPM typically will conclude that a call should be placed to a healthcare provider if a patient has bleeding signs or symptoms, clotting signs or symptoms, changes in diet, vitamins or other medications, as well as if the patient shows signs of illness, or has experienced vomiting and/or diarrhea. If the CPM determines that a call should be placed, the CPM is configured to initiate the call and establish voice communications and/or exchange data with the healthcare provider via a communications network (Block 1850).

If the answer at Block 1800 is "No", the CPM assesses the need to adjust the patient's medication dosage (e.g., warfarin for anticoagulation therapy) (Block 1900). If the CPM determines that a patient's medication dosage should be adjusted, an algorithm stored within the CPM is used to modify the medication dosage (Block 1950). The patient is notified of the medication dosage adjustment and is prompted to administer the medication under the modified dosage (Block 1951).

The CPM then determines whether the patient's self-testing (e.g., PT test) schedule should be adjusted based on available patient data or prior self-test results (Block 2000). If the answer is "Yes", the patient's self-testing schedule is adjusted (Block 2050). Operations then return to Block 2100). If the answer at Block 2000 is "No", a determination is made whether a routine data transfer is scheduled (Block 2075). If the answer is "Yes", patient information is transmitted to a PAC server according to schedule (Block 2100) as described above.

As is well known to those having skill in the art, a warfarin adjusting algorithm relies on a target range for PT test results specified by a healthcare provider. At the start of therapy, the desired PT test target range and patient's current weekly and daily warfarin dosage levels are input, along with parameters that specify how changes in warfarin doses are to be calculated. In the absence of serious symptom reports, deviations in PT test results from the patient's specified target range are corrected by a change in warfarin doses, utilizing physician-prescribed adjustment parameters. Small deviations from the target PT range in previously stable patients are corrected by transient or bolus dosage adjustments. Depending upon the magnitude of the total amount of warfarin that must be added or subtracted from the weekly does, either one- or two-day medication alterations are made. Somewhat larger deviations from the target PT range that are unaccompanied by dangerous symptom reports are corrected by the algorithm using a combination of an immediate change (positive or negative bolus) and a permanent change in the weekly basal dose.

Changed weekly doses are spread across days according to a dosing schedule that may result in the different doses being taken on even and odd days of the week. This is desirable because patients cannot be expected to have an indefinite number of different warfarin formulations (pill strengths) available, and it is possible because the half-life of the major ingredient in Warfarin that affects PT is 48 to 72 hours. A CPM transparently calculates dosage changes and divides the total weekly basal dose into a recommended daily dose informed by immediately available medications. Warfarin pills may be scored and, thus, may be cut in half if necessary. If new dosing requirements cannot be met with an available supply of warfarin, the CPM instructs the patient to transmit a request for another formulation of warfarin to be prescribed.

Computer code within a CPM may be configured to prompt a patient to place the device in a dedicated modem cradle and initiate an IP link on both a scheduled and contingent basis. A CPM can utilize secure socket layer (SSL) internet protocols for two-way communication with a data processing system of a healthcare provider or other third party. A CPM may be uniquely identified during the communications session. Patient home-collected data are automatically uploaded and screened, and any newly available self-monitoring or prescriptive parameters are automatically downloaded to the CPM during the session. Both programmed and personalized messages can also be sent to a patient to enhance compliance with the treatment or self-care regimen.

A CPM according to the present invention may be utilized within a system utilizing a PAC server as described above. PAC server features that support remote management of insulin therapy are well suited for anticoagulation therapy with warfarin, as well as for a wide range of disease therapies. The PAC specification supports automated voice message delivery that can be used to prompt patients to make appointments, return calls or connect their CPM with a PAC server to obtain an updated warfarin management prescription.

Patient data uploaded to a PAC server (Block 2100, FIG. 15) can be screened in real-time for serious data (signs, symptoms or conditions) and individualized deviations from specified physiologic levels. Serious data (signs, symptoms or conditions), when detected, can contingently trigger paging of appropriate medical personnel on an as needed basis. Patient problems can be hierarchically prioritized by severity, and can contingently trigger software-initiated alarms for immediate review by healthcare professionals. Problems such as failure to transfer data on schedule and poor compliance with taking or recording prescribed warfarin doses can also be identified. In the absence of problems a PAC server can also schedule semi-automated periodic routine case reviews that document patient progress and can provide supportive feedback delivered using email.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A system that monitors anticoagulation therapy of a patient, wherein the anticoagulation therapy includes a patient-administered medication regimen selected from the group consisting of warfarin and vitamin K antagonists, heparin and glucosaminoglycans, and direct thrombin inhibitors, and a patient-administered regimen for a coagulation test that monitors efficacy of the medication regimen, wherein the coagulation test is selected from the group consisting of prothrombin time (PT) test, partial thromboplastin time (PTT) test, activated clotting time (ACT) test, heparin assays, ecarin clotting time (ECT) test, and thrombin clotting time test, wherein the system comprises:

a portable patient apparatus, comprising:
a processor;
a user interface in communication with the processor;
computer code executable by the processor that receives and stores data from a patient, wherein the patient data includes at least one of physiological data, pathophysiological data, biological data, psychological data, neuropsychological data, and behavioral data;
computer code executable by the processor that assesses severity of the received patient data;
computer code executable by the processor that prompts the patient via the user interface to perform a patient-administered coagulation test if the received patient data are assessed to be above a threshold severity level;
computer code executable by the processor that receives and stores coagulation test results from the patient-administered coagulation test; and
computer code executable by the processor that communicates the received coagulation test results from the patient-administered coagulation test to a healthcare provider via a communications network; and a remotely located data processing system configured to communicate with and receive data from the portable patient apparatus, the remotely located data processing system comprising:
computer code that obtains patient data from the patient apparatus;
computer code that analyzes the obtained patient data from to identify medical conditions of a patient;
computer code that displays identified patient medical conditions for a patient in selectable, prioritized order according to medical severity via a remotely located client in communication with the central data processing system; and
computer code that displays treatment options for treating a selected medical condition for a patient.

2. The system according to claim 1 wherein the portable patient apparatus further comprises:
computer code executable by the processor that assesses severity of the received coagulation test results from the patient-administered coagulation test;
computer code executable by the processor that modifies the patient-administered medication regimen if the received coagulation test results from the patient-administered coagulation test are assessed to be above a threshold severity level; and
computer code executable by the processor that communicates the modified patient-administered medication regimen to the patient.

3. The system according to claim 1 further comprising computer code that communicates treatment information from the remotely located data processing system to the patient apparatus.

4. The system according to claim 3 wherein the computer code that communicates treatment information from the remotely located data processing system to the portable patient apparatus comprises computer code that transmits treatment information via wireless, satellite, telephone, e-mail, AVM or facsimile transmission.

5. The system according to claim 4 wherein the computer code that communicates treatment information from the remotely located data processing system to the portable patient apparatus comprises computer code that modifies the medication algorithm within the portable patient apparatus.

6. The system according to claim 1 wherein the computer code that obtains patient data from the portable patient apparatus further comprises:
   computer code that analyzes data transmitted from the patient apparatus substantially simultaneously with the transmission thereof to the remotely located data processing system to identify emergency medical conditions requiring immediate medical attention; and
   computer code that automatically communicates treatment information to the patient apparatus for an identified emergency medical condition.

7. The system according to claim 1 wherein the remotely located data processing system further comprises:
   computer code that monitors patient usage of medication; and
   computer code that orders medication for a patient from a supplier of medication.

8. The system according to claim 1 wherein the computer code that displays identified patient medical conditions comprises computer code that displays selected ones of the identified patient medical conditions.

9. The system according to claim 1 wherein the portable patient apparatus further comprises computer code that receives information via the user interface about patient compliance with the patient-administered medication regimen and the patient-administered coagulation test regimen during a preceding time period.

10. The system according to claim 1 wherein the portable patient apparatus further comprises computer code that communicates information regarding medication dosage to a patient via the user interface in response to determining that a patient did not comply with the patient-administered medication regimen in a preceding time period.

* * * * *